(12) United States Patent
Lyons et al.

(10) Patent No.: US 9,592,089 B2
(45) Date of Patent: Mar. 14, 2017

(54) METHOD OF ASSEMBLING A SPRING-LOADED MECHANISM OF A SURGICAL INSTRUMENT

(71) Applicant: Covidien LP, New Haven, CT (US)

(72) Inventors: Michael B. Lyons, Boulder, CO (US); Grant T. Sims, Littleton, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/858,397

(22) Filed: Sep. 18, 2015

(65) Prior Publication Data

US 2016/0008056 A1 Jan. 14, 2016

Related U.S. Application Data

(63) Continuation of application No. 14/036,238, filed on Sep. 25, 2013, which is a continuation-in-part of application No. 13/461,335, filed on May 1, 2012.

(51) Int. Cl.
*A61B 18/14* (2006.01)
*A61B 17/28* (2006.01)
(Continued)

(52) U.S. Cl.
CPC ...... *A61B 18/1445* (2013.01); *A61B 17/2812* (2013.01); *A61B 90/03* (2016.02);
(Continued)

(58) Field of Classification Search
CPC ........ A61B 18/1445; A61B 2017/2936; A61B 2017/00526; A61B 2017/00367;
(Continued)

(56) References Cited

U.S. PATENT DOCUMENTS 2,801,633 A 8/1957 Ehrlich
3,522,809 A 8/1970 Cornell
(Continued)

FOREIGN PATENT DOCUMENTS

EP 0584787 A1 3/1994
EP 2347725 A1 7/2011
(Continued)

OTHER PUBLICATIONS

Extended European Search Report from Appl. No. EP 14186184.9 dated Feb. 9, 2015.
(Continued)

*Primary Examiner* — Sarang Afzali

(57) ABSTRACT

A method of assembling a surgical instrument includes inserting a knife into a knife guide and positioning the knife and the knife guide within an inner shaft. The method also includes moving a drive collar stop along a longitudinal axis defined through the inner shaft, engaging a pair of opposing projections of the drive collar stop within a corresponding first pair of opposing apertures defined in the inner shaft, and moving a drive collar along the inner shaft. The method also includes moving a spring along the inner shaft, compressing the spring, moving an inner shaft stop transverse to the longitudinal axis defined through the inner shaft, and engaging a pair of opposing projections of the inner shaft stop within a corresponding second pair of opposing apertures defined in the inner shaft proximal to the first pair of opposing apertures.

4 Claims, 22 Drawing Sheets

(51) Int. Cl.
*A61B 17/00* (2006.01)
*A61B 17/29* (2006.01)
*A61B 18/00* (2006.01)

(52) U.S. Cl.
CPC ............ *A61B 2017/00367* (2013.01); *A61B 2017/00526* (2013.01); *A61B 2017/2936* (2013.01); *A61B 2018/0063* (2013.01); *A61B 2018/00619* (2013.01); *A61B 2018/1455* (2013.01); *A61B 2090/033* (2016.02); *A61B 2090/034* (2016.02); *Y10T 29/49002* (2015.01); *Y10T 29/49826* (2015.01)

(58) Field of Classification Search
CPC ...... A61B 2018/0063; A61B 2019/304; A61B 2018/1455; A61B 2019/303; A61B 18/1442; A61B 18/1447; A61B 2018/145; A61B 2018/1452; A61B 2018/1457; A61B 2017/2926; A61B 2017/2933; A61B 2017/2934; A61B 2017/2937; Y10T 29/49826; Y10T 29/49002
See application file for complete search history.

(56) References Cited

U.S. PATENT DOCUMENTS

| | | |
|---|---|---|
| 5,383,471 A | 1/1995 | Funnell |
| 5,486,189 A | 1/1996 | Mudry et al. |
| 5,591,188 A | 1/1997 | Waisman |
| 5,707,392 A | 1/1998 | Kortenbach |
| 6,117,158 A | 9/2000 | Measamer et al. |
| 8,333,765 B2 | 12/2012 | Johnson et al. |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 2002/0058925 A1 | 5/2002 | Kaplan et al. |
| 2004/0254573 A1 | 12/2004 | Dycus et al. |
| 2009/0182327 A1 | 7/2009 | Unger |
| 2010/0082041 A1 | 4/2010 | Prisco |
| 2011/0009864 A1 | 1/2011 | Bucciaglia et al. |
| 2012/0226276 A1 | 9/2012 | Dycus |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0283734 A1 | 11/2012 | Ourada |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296332 A1 | 11/2012 | Chernov et al. |
| 2012/0296333 A1 | 11/2012 | Twomey |
| 2012/0296334 A1 | 11/2012 | Kharin |
| 2012/0296371 A1 | 11/2012 | Kappus et al. |
| 2012/0303021 A1 | 11/2012 | Guerra et al. |
| 2012/0303025 A1 | 11/2012 | Garrison |
| 2012/0303026 A1 | 11/2012 | Dycus et al. |
| 2012/0310240 A1 | 12/2012 | Olson et al. |
| 2012/0316601 A1 | 12/2012 | Twomey |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0014375 A1 | 1/2013 | Hempstead et al. |
| 2013/0018364 A1 | 1/2013 | Chernov et al. |
| 2013/0018371 A1 | 1/2013 | Twomey |
| 2013/0018372 A1 | 1/2013 | Sims et al. |
| 2013/0022495 A1 | 1/2013 | Allen, IV et al. |
| 2013/0041370 A1 | 2/2013 | Unger |
| 2013/0041402 A1 | 2/2013 | Chojin et al. |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066303 A1 | 3/2013 | Hart |
| 2013/0066318 A1 | 3/2013 | Kerr |
| 2013/0071282 A1 | 3/2013 | Fry |
| 2013/0072919 A1 | 3/2013 | Allen, IV et al. |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0082035 A1 | 4/2013 | Allen, IV et al. |
| 2013/0085491 A1 | 4/2013 | Twomey et al. |
| 2013/0085496 A1 | 4/2013 | Unger et al. |
| 2013/0085516 A1 | 4/2013 | Kerr et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0150842 A1 | 6/2013 | Nau, Jr. et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |
| 2013/0218198 A1 | 8/2013 | Larson et al. |
| 2013/0226177 A1 | 8/2013 | Brandt et al. |
| 2013/0226178 A1 | 8/2013 | Brandt et al. |
| 2013/0232753 A1 | 9/2013 | Ackley et al. |
| 2013/0238016 A1 | 9/2013 | Garrison |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0270322 A1 | 10/2013 | Scheib et al. |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296848 A1 | 11/2013 | Allen, IV et al. |
| 2013/0296854 A1 | 11/2013 | Mueller |
| 2013/0296856 A1 | 11/2013 | Unger et al. |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |

FOREIGN PATENT DOCUMENTS

| | | |
|---|---|---|
| WO | 2010/014825 A1 | 2/2010 |
| WO | 2010/114634 A1 | 10/2010 |

(56) References Cited

FOREIGN PATENT DOCUMENTS

OTHER PUBLICATIONS

International Search Report No. 13166214.0 dated Dec. 4, 2013.
Chinese office action and English language translation issued in application No. 201310153890.5 on Mar. 1, 2016.

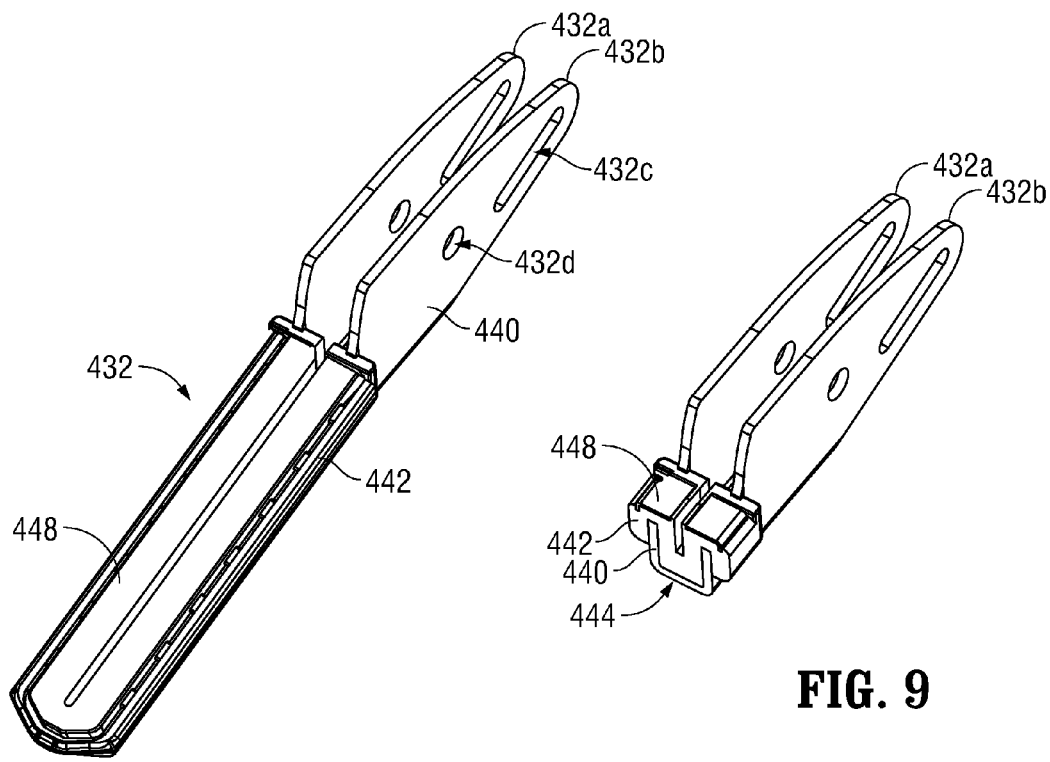
FIG. 8
FIG. 9
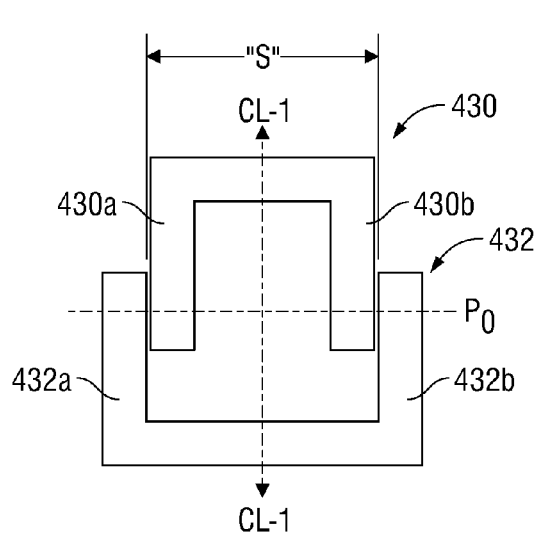
FIG. 10
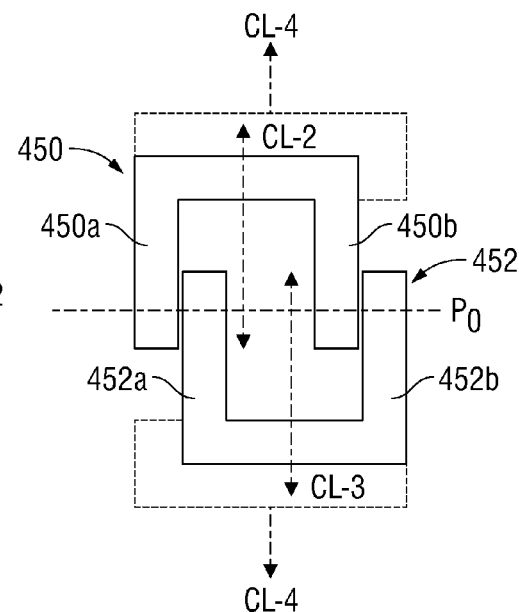
FIG. 11

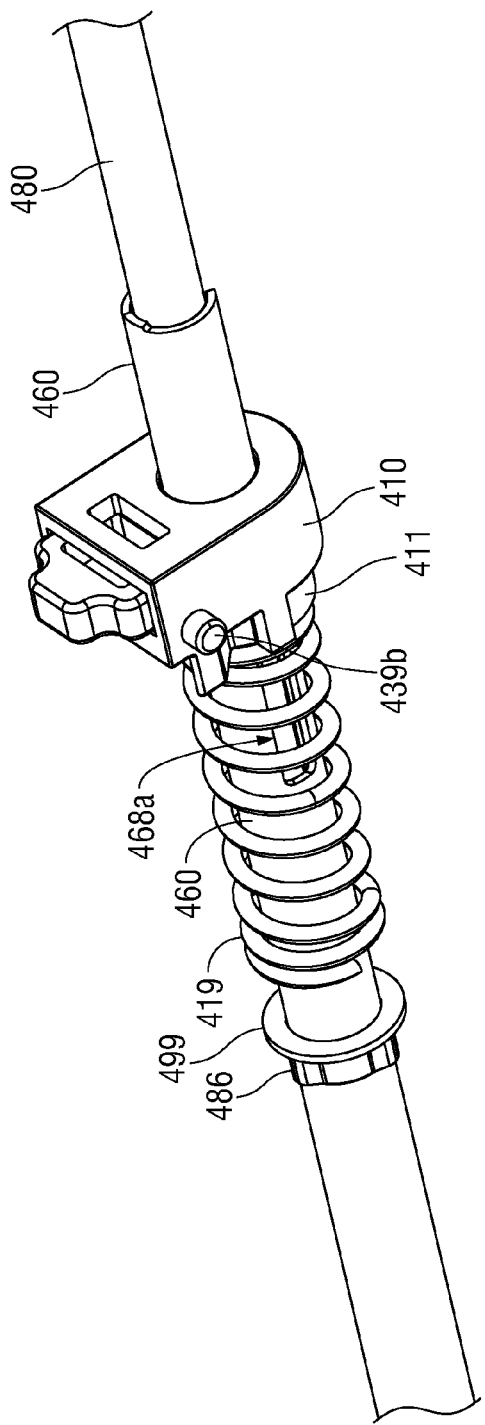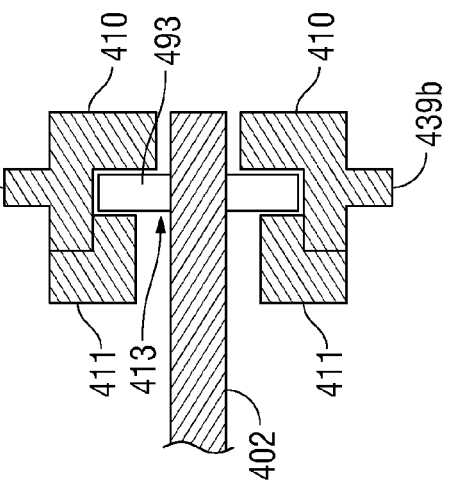
FIG. 14A
FIG. 14B

METHOD OF ASSEMBLING A SPRING-LOADED MECHANISM OF A SURGICAL INSTRUMENT

CROSS-REFERENCE TO RELATED APPLICATIONS

This application is a continuation of U.S. patent application Ser. No. 14/036,238, filed on Sep. 25, 2013, which is a continuation-in-part of U.S. patent application Ser. No. 13/461,335, filed on May 1, 2012.

BACKGROUND

1. Technical Field

The present disclosure relates generally to the field of surgical instruments. In particular, the disclosure relates to an endoscopic electrosurgical forceps that is economical to manufacture and is capable of sealing and cutting relatively large tissue structures. The present disclosure relates also to connection mechanisms to actuate the jaw members of a surgical instrument.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 $kg/cm^2$ to about 16 $kg/cm^2$.

Additionally, prior art surgical instruments include connection mechanisms for actuation of distal end components such as jaw members where the connection mechanisms require several manufacturing steps such as attaching a mandrel to an inner shaft member with corresponding number of parts required. Misalignment of the parts may result in an inconsistent and/or inadequate delivery of the shaft force required for actuation.

As is traditional, the term "distal" refers herein to an end of the apparatus that is farther from an operator, and the term "proximal" refers herein to the end of the electrosurgical forceps that is closer to the operator.

SUMMARY

The present disclosure relates to an electrosurgical apparatus and methods for performing electrosurgical procedures. More particularly, the present disclosure relates to electrosurgically sealing tissue.

The present disclosure describes a surgical instrument for treating tissue that is economical to manufacture and is capable of sealing and cutting relatively large tissue structures.

The surgical instrument includes an elongated shaft having a distal portion and a proximal portion coupled to a housing. The elongated shaft defines a longitudinal axis. An inner shaft member extends at least partially through the elongated shaft. The inner shaft member is selectively movable in a longitudinal direction with respect to the elongated shaft. An end effector adapted for treating tissue is supported by the distal portion of the elongated shaft. The end effector includes upper and lower jaw members pivotally coupled to the distal portion of the elongated shaft about a pivot axis. The upper and lower jaw members include a first and second pair of laterally spaced flanges, respectively. The first and second pairs of flanges of the jaw members are arranged in an offset configuration such that one flange of the upper jaw member is positioned on a laterally exterior side of a corresponding flange of the lower jaw member, and the other flange of the upper jaw member is positioned on a laterally interior side of the other flange of the lower jaw member.

Additionally or alternatively, the housing includes a movable actuating mechanism configured to cause longitudinal movement of the inner shaft member relative to the elongated shaft.

Additionally or alternatively, the elongated shaft includes at least one feature formed therein configured to operably engage the movable actuating mechanism.

Additionally or alternatively, the elongated shaft has a generally circular profile joined along two opposing longitudinal edges.

Additionally or alternatively, the two opposing longitudinal edges are laser welded together.

Additionally or alternatively, the two opposing longitudinal edges are joined by one of a box joint interface and a dovetail joint interface.

Additionally or alternatively, the surgical instrument includes a cam pin supported by the inner shaft member such that longitudinal movement of the inner shaft member is imparted to the cam pin.

Additionally or alternatively, each of the first and second laterally spaced flanges define a camming slot for engaging the cam pin.

Additionally or alternatively, the upper and lower jaw members are constructed as substantially identical components positioned in a laterally offset manner with respect to one another.

Additionally or alternatively, the pivot axis extends through each of the flanges in a direction substantially transverse to the longitudinal axis.

Additionally or alternatively, the inner shaft member extends through the jaw members on a laterally interior side of each of the flanges.

Additionally or alternatively, the surgical instrument includes a knife selectively movable in a longitudinal direction with respect to the inner shaft member.

Additionally or alternatively, the inner shaft member includes a knife guide disposed on a distal end of the inner shaft member such that the knife is substantially surrounded on four lateral sides.

According to another aspect of the present disclosure, a surgical instrument is provided. The surgical instrument includes an elongated shaft including a distal portion and a proximal portion coupled to a housing. The elongated shaft defines a longitudinal axis. An end effector adapted for treating tissue is supported by the distal portion of the elongated shaft. The end effector includes first and second jaw members pivotally coupled to one another to move between open and closed configurations. Each of the jaw members includes a pair of laterally spaced flanges. Each of the flanges includes a camming surface. A knife extends at least partially through the elongated shaft and is selectively movable in a longitudinal direction between the flanges of the jaw members. A blade of the knife is extendable into a tissue contacting portion of the jaw members. An inner shaft member extends at least partially through the elongated shaft and is selectively movable in a longitudinal direction with respect to the knife and with respect to the elongated shaft. The inner shaft member carries a cam pin positioned to engage the camming surface of each of the flanges to induce the jaw members to move between the open and closed configurations.

Additionally or alternatively, the elongated shaft includes at least one feature defined therein configured to engage a movable actuating mechanism operably associated with the housing.

Additionally or alternatively, the laterally spaced flanges of the jaw members are arranged in a nestled configuration wherein both of the flanges of one of the jaw members are arranged within a laterally interior side of the laterally spaced flanges of the other of the jaw members.

According to another aspect of the present disclosure, a method of manufacturing a surgical device including a housing and an elongated shaft for coupling an end effector with the housing of the surgical device is provided. The method includes the steps of stamping at least one feature into a blank of sheet metal and folding the blank into such that two opposing longitudinal edges of the blank meet at a longitudinal seam to form an elongated shaft. The method also includes the step of operably coupling an end effector to at least one feature formed at a distal portion of the elongated shaft. The method also includes the step of engaging at least one actuating mechanism supported by a housing with at least one feature formed at a proximal portion of the elongated shaft to operably couple the proximal portion of the elongated shaft with the housing. The actuating mechanism is configured to selectively move the end effector between an open position and a closed position.

Additionally or alternatively, the method includes the step of joining the two opposing longitudinal edges along the longitudinal seam.

Additionally or alternatively, the joining step further comprises laser welding the longitudinal seam. The longitudinal seam may be a box joint configuration or a dovetail joint configuration.

Additionally or alternatively, the method includes the step of coupling a drive rod to the at least one actuating mechanism at a proximal end and to the end effector at a distal end. The drive rod may be configured to translate within and relative to the elongated shaft upon movement of the at least one actuation mechanism to effect actuation of the end effector.

Additionally or alternatively, the method includes the step of stamping at least one feature at a distal end of the blank such that a clevis is formed at a distal end of the elongated shaft. The clevis may be configured to support the end effector.

According to another aspect of the present disclosure, a connection mechanism for a surgical instrument is provided. The connection mechanism includes an inner shaft member that is configured to extend at least partially through an elongated shaft member of a surgical instrument and that defines proximal and distal ends. The inner shaft member is selectively movable in a longitudinal direction with respect to the elongated shaft member. The inner shaft member includes at least one aperture defined therein and that extends partially along the longitudinal direction of the inner shaft member and that is disposed distally from the proximal end. The inner shaft member is configured to enable a drive collar member to slide on the inner shaft member and reciprocate along the longitudinal direction of the inner shaft member. A drive collar stop member is disposed to slide on the inner shaft member and to move along the longitudinal direction of the inner shaft member. The drive collar stop member moves in a direction relative to the longitudinal axis defined by the inner shaft member to engage the at least one aperture and limit further longitudinal motion of the drive collar member.

Additionally or alternatively, the connection mechanism may further include a drive collar member disposed to slide on the inner shaft member, wherein the drive collar member is movable along the longitudinal direction of the inner shaft member, and wherein the drive collar member is configured such that further longitudinal motion of the drive collar member is limited upon engagement of the drive collar stop member with the at least one aperture.

Additionally or alternatively, the inner shaft member may include at least one additional aperture defined therein and that extends partially along the longitudinal direction of the inner shaft member and that is disposed proximally of the at least one aperture. The at least one additional aperture is configured to enable an inner shaft stop member to slide on the inner shaft member and to move along the longitudinal direction. The at least one additional aperture may be configured to enable the inner shaft stop member to engage and limit movement of the inner shaft member along the longitudinal axis following insertion of a spring member on the inner shaft member between the drive collar member and the inner shaft stop member.

Additionally or alternatively, the connection mechanism may further include a spring member inserted on the inner shaft member between the drive collar member and the inner shaft stop member.

Additionally or alternatively, an inner shaft stop member may be disposed to slide on the inner shaft member and is movable along the longitudinal direction. The inner shaft stop member is disposed proximally of the drive collar member. The inner shaft stop member engages the at least one additional aperture to limit movement of the inner shaft member along the longitudinal axis following insertion of the spring member on the inner shaft member between the drive collar member and the inner shaft stop member.

Additionally or alternatively, the spring member defines a proximal end and a distal end, and the drive collar member may further include a projection extending proximally from the drive collar member and that is configured to engage within an aperture defined in the distal end of the spring member when the spring member is inserted on the inner shaft member between the drive collar member and the inner shaft stop member.

Additionally or alternatively, the inner shaft stop member further includes a projection that extends distally from the inner shaft stop member and that is configured to engage within an aperture defined in the proximal end of the spring member when the spring member is inserted on the inner shaft member between the drive collar member and the inner shaft stop member.

Additionally or alternatively, the inner shaft member defines a first cross-sectional area. The drive collar stop member defines a central aperture having a second cross-sectional area exceeding the first cross-sectional area. The second cross-sectional area defines an upper portion of the second cross-sectional area and a lower portion of the second cross-sectional area. The drive collar stop member defines at least one projection projecting inwardly within the upper portion of the second cross-sectional area to reduce the upper portion of the second cross-sectional area as compared to the lower portion of the second cross-sectional area, and thereby the drive collar stop member retains the inner shaft member in the lower portion of the second cross-sectional area as the drive collar stop member moves distally along the longitudinal direction.

Additionally or alternatively, when the drive collar stop member moves distally along the longitudinal direction to the at least one distal aperture defined in the inner shaft member, the drive collar stop member shifts in a direction relative to the longitudinal axis to a position wherein at least one projection engages with the at least one aperture and moves to a position within the at least one aperture to limit further longitudinal motion of the drive collar member in the direction of the proximal end of the inner shaft member.

Additionally or alternatively, the drive collar stop member defines at least one portion having a weight density differing from at least another portion having another weight density, and the shift of the drive collar stop member relative to the longitudinal axis is effected by the difference in weight densities.

Additionally or alternatively, the inner shaft stop member defines an aperture and at least one projection that projects inwardly within the aperture, the aperture imparting a generally U-shaped configuration to the inner shaft stop member. The at least one projection that projects inwardly within the aperture effects the engaging of the at least one additional aperture disposed proximally of the drive collar member.

According to another aspect of the present disclosure, a method of manufacturing a connection mechanism for a surgical instrument is provided. The method includes moving a drive collar stop member longitudinally along an inner shaft member, engaging the drive collar stop member in at least one aperture defined in the inner shaft member to limit further longitudinal movement of the drive collar stop member, and moving a drive collar member longitudinally along the inner shaft member until the drive collar stop member limits further longitudinal movement of the drive collar member.

Additionally or alternatively, the method of manufacturing may further include inserting, in a compressed configuration, a spring member on the inner shaft member; and moving the spring member longitudinally along the inner shaft member to contact the drive collar member to limit further longitudinal movement of the spring member.

Additionally or alternatively, the method of manufacturing may further include moving an inner shaft stop member in a direction relative to the longitudinal movement of the drive collar stop member along the inner shaft member, and engaging the inner shaft stop member in at least one additional aperture defined in the inner shaft member to limit longitudinal movement of the inner shaft stop member when the spring member contacts the inner shaft stop member upon extending from the compressed configuration.

Additionally or alternatively, the step of engaging the drive collar stop member in at least one aperture defined in the inner shaft member to limit further longitudinal movement of the drive collar stop member includes moving the drive collar stop member in a direction relative to the longitudinal movement of the drive collar stop member to engage with the at least one aperture defined in the inner shaft member to limit further longitudinal movement of the drive collar stop member.

Additionally or alternatively, the step of engaging the inner shaft stop member in at least one aperture defined in the inner shaft member to limit further longitudinal movement of the inner shaft stop member includes moving the inner shaft stop member in the direction of the longitudinal movement of the drive collar member to engage with the at least one aperture defined in the inner shaft member to limit further longitudinal movement of the inner shaft member.

Additionally or alternatively, the method of manufacturing may further include engaging a projection extending proximally from the drive collar member within an aperture defined in a distal end of the spring member when the spring member is inserted on the inner shaft member between the drive collar member and the inner shaft stop member.

Additionally or alternatively, the method of manufacturing may further include engaging a projection extending distally from the inner shaft stop member within an aperture defined in a proximal end of the spring member when the spring member is inserted on the inner shaft member between the drive collar member and the inner shaft stop member.

Additionally or alternatively, the method of manufacturing may further include retaining the inner shaft member in a portion of an aperture defined in the drive collar stop member as the drive collar stop member moves distally along the longitudinal direction of the inner shaft member.

Additionally or alternatively, the method of manufacturing may further include limiting further longitudinal motion of the drive collar member in the direction of the proximal end of the inner shaft member by engaging the drive collar stop member with the at least one aperture defined in the inner shaft member.

Additionally or alternatively, the engaging by the drive collar stop member with the at least one aperture is effected by shifting the drive collar stop member in a direction relative to the longitudinal movement of the drive collar stop member.

Additionally or alternatively, the drive collar stop member defines at least one portion having a weight density differing from at least another portion having another weight density, and the shifting of the drive collar stop member is effected by the difference in weight densities.

Additionally or alternatively, the method of manufacturing may further include defining an aperture in the inner shaft stop member to impart a generally U-shaped configuration to the inner shaft stop member, and defining at least one projection projecting inwardly within the aperture defined in the inner shaft stop member, wherein the engaging of the at least one additional aperture disposed proximally of the drive collar member by the inner shaft stop member is effected by engaging the at least one projection projecting inwardly within the aperture defined in the inner shaft stop member with the at least one additional aperture disposed proximally of the drive collar member.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 8 is a perspective view of a lower jaw member of the end effector of FIG. 1 depicting a double flag at a proximal end thereof;

FIG. 9 is a cross-sectional, perspective view of the lower jaw member of FIG. 8;

FIG. 10 is a schematic view of the nestled arrangement of the double flag of FIG. 8 with a double flag of an upper jaw member;

FIG. 11 is a schematic view of an alternative offset arrangement of double flags of an alternate pair of jaw members;

FIG. 14A is a perspective view of a proximal portion of the knife actuation mechanism of the end effector of FIG. 1;

FIG. 14B is a cross-sectional, top view of a knife collar of the knife actuation mechanism of the end effector of FIG. 1;

DETAILED DESCRIPTION

Figure 1:
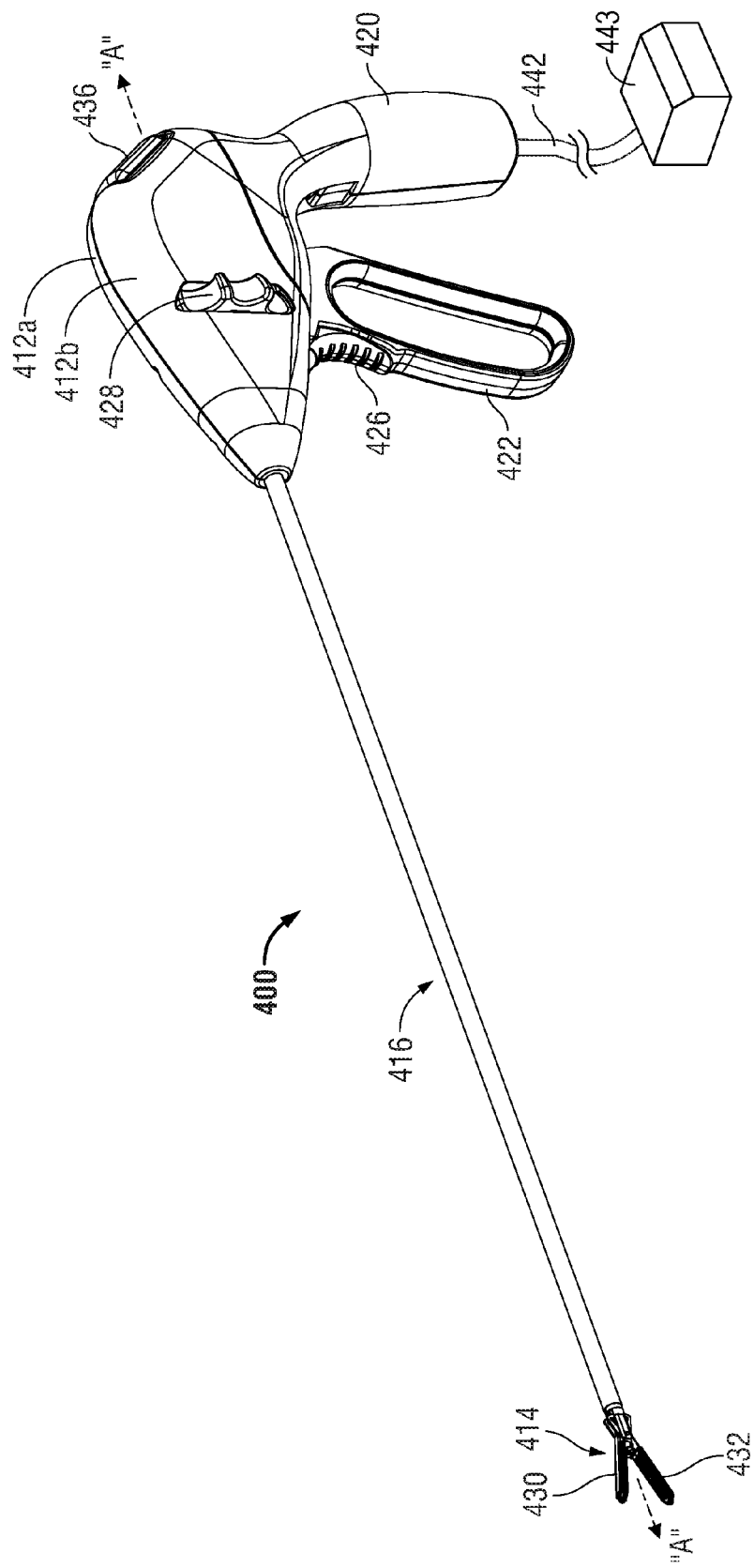
FIG. 1 is a perspective view of an electrosurgical forceps according to an embodiment of the present disclosure including a housing, an elongated shaft, and an end effector.

Referring initially to FIG. 1, an embodiment of an electrosurgical forceps 400 generally includes a housing 412 that supports various actuators thereon for remotely controlling an end effector 414 through an elongated shaft 416. Although this configuration is typically associated with instruments for use in laparoscopic or endoscopic surgical procedures, various aspects of the present disclosure may be practiced with traditional open instruments and in connection with endoluminal procedures as well.

The housing 412 is constructed of a left housing half 412a and a right housing half 412b. The left and right designation of the housing halves 412a, 412b refer to the respective directions as perceived by an operator using the forceps 400. The housing halves 412a, 412b may be constructed of sturdy plastic, and may be joined to one another by adhesives, ultrasonic welding or other suitable assembly methods.

To mechanically control the end effector 414, the housing 412 supports a stationary handle 420, a movable handle 422, a trigger 426 and a rotation knob 428. The movable handle 422 is operable to move the end effector 414 between an open configuration (FIG. 2A) wherein a pair of opposed jaw members 430, 432 are disposed in spaced relation relative to one another, and a closed or clamping configuration (FIG. 2B) wherein the jaw members 430, 432 are closer together. Approximation of the movable handle 422 with the stationary handle 420 serves to move the end effector 414 to the closed configuration and separation of the movable handle 422 from the stationary handle 420 serves to move the end effector 414 to the open configuration. The trigger 426 is operable to extend and retract a knife blade 456 (see FIGS. 2A and 2B) through the end effector 414 when the end effector 414 is in the closed configuration. The rotation knob 428 serves to rotate the elongated shaft 416 and the end effector 414 about a longitudinal axis A-A extending through the forceps.

To electrically control the end effector 414, the housing 412 supports a switch 436 thereon, which is operable by the user to initiate and terminate the delivery of electrosurgical energy to the end effector 414. The switch 436 is in electrical communication with a source of electrosurgical energy such as electrosurgical generator 443 or a battery (not shown) supported within the housing 412. The generator 443 may include devices such as the LIGASURE® Vessel Sealing Generator and the Force Triad® Generator as sold by Covidien Energy-based Devices of Boulder, Colo. A cable 442 extends between the housing 412 and the generator 443 and may include a connector (not shown) thereon such that the forceps 400 may be selectively coupled and decoupled electrically from the generator 443.

Figure 2A:
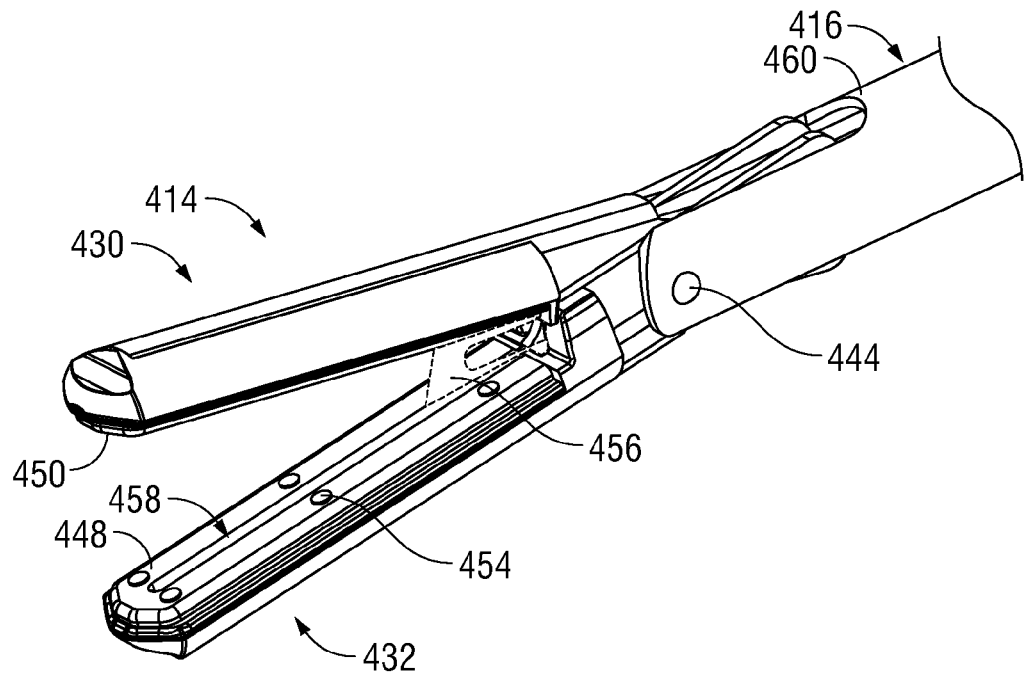
FIG. 2A is an enlarged perspective view of the end effector of FIG. 1 depicted with a pair of jaw members in an open configuration.
Figure 2B:
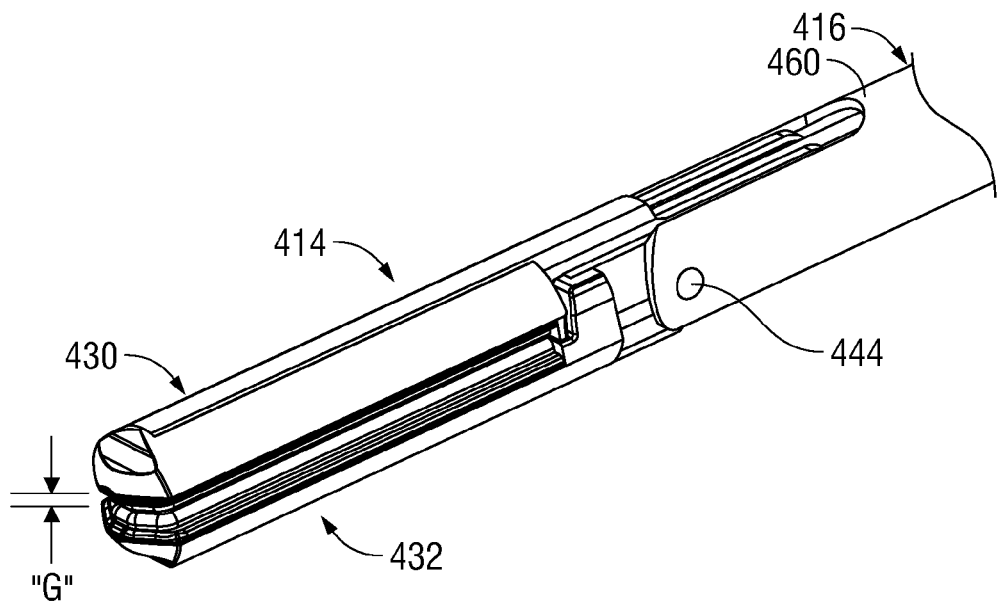
FIG. 2B is an enlarged perspective view of the end effector of FIG. 1 depicted with the pair of jaw members in a closed configuration.

Referring now to FIGS. 2A-3, the end effector 414 may be moved from the open configuration (FIG. 2A) wherein tissue (not shown) is received between the jaw members 430, 432, and the closed configuration (FIG. 2B), wherein the tissue is clamped and sealed. Upper jaw member 430 and lower jaw member 432 are mechanically coupled to the elongated shaft 416 about a pivot pin 444. The upper and lower jaw members 430, 432 are electrically coupled to cable 442, and thus to the generator 443 (e.g., via a respective wire extending through the elongated shaft 416) to provide an electrical pathway to a pair of electrically conductive, tissue-engaging sealing plates 448, 450 disposed on the lower and upper jaw members 432, 430, respectively. A pair of wire conduits 478a and 478b may be provided to guide wires proximally from the end effector 414. The wire conduits 478a and 478b may be constructed of a plastic tube, and serve to protect wires from sharp edges that may form on surrounding components. The sealing plate 448 of the lower jaw member 432 opposes the sealing plate 450 of the upper jaw member 430, and, in some embodiments, the sealing plates 448 and 450 are electrically coupled to opposite terminals, e.g., positive or active (+) and negative or return (−) terminals associated with the generator 443. Thus, bipolar energy may be provided through the sealing plates 448 and 450. Alternatively, the sealing plates 448 and 450 and/or the end effector 414 may be configured for delivering monopolar energy to the tissue. In a monopolar configuration, the one or both sealing plates 448 and 450 deliver electrosurgical energy from an active terminal, e.g. (+), while a return pad (not shown) is placed generally on a patient and provides a return path to the opposite terminal, e.g. (−), of the generator 443.

The jaw members 430, 432 may be pivoted about the pivot pin 444 to move the end effector 414 to the closed configuration of FIG. 2B wherein the sealing plates 448, 450 provide a pressure to tissue grasped therebetween. In some embodiments, to provide an effective seal, a pressure within a range between about 3 kg/cm$^2$ to about 16 kg/cm$^2$ and, desirably, within a working range of 7 kg/cm$^2$ to 13 kg/cm$^2$ is applied to the tissue. Also, in the closed configuration, a separation or gap distance "G" may be maintained between the sealing plates 448, 450 by an array of stop members 454 (FIG. 2A) disposed on or adjacent the sealing plates 448, 450. The stop members 454 contact opposing surfaces on the opposing jaw member 430, 432 and prohibit further approximation of the sealing plates 448, 450. In some embodiments, to provide an effective tissue seal, an appropriate gap distance of about 0.001 inches to about 0.010 inches and, desirably, between about 0.002 and about 0.005 inches may be provided. In some embodiments, the stop members 454 are constructed of an electrically non-conductive plastic or other material molded onto the jaw members 430, 432, e.g., by a process such as overmolding or injection molding. In other embodiments, the stop members 454 are constructed of a heat-resistant ceramic deposited onto the jaw members 430, 432.

Electrosurgical energy may be delivered to the tissue through the electrically conductive seal plates 448, 450 to effect a tissue seal. Once a tissue seal is established, a knife blade 456 may be advanced through a knife channel 458 defined in one or both jaw members 430, 432 to transect the sealed tissue. Knife blade 456 is depicted in FIG. 2A as extending from the elongated shaft 416 when the end effector 414 is in an open configuration. In some embodiments, a knife lockout is provided to prevent extension of the knife blade 456 into the knife channel 458 when the end effector 414 is in the open configuration, thus preventing accidental or premature transection of tissue and avoiding safety concerns.

Figure 3A:
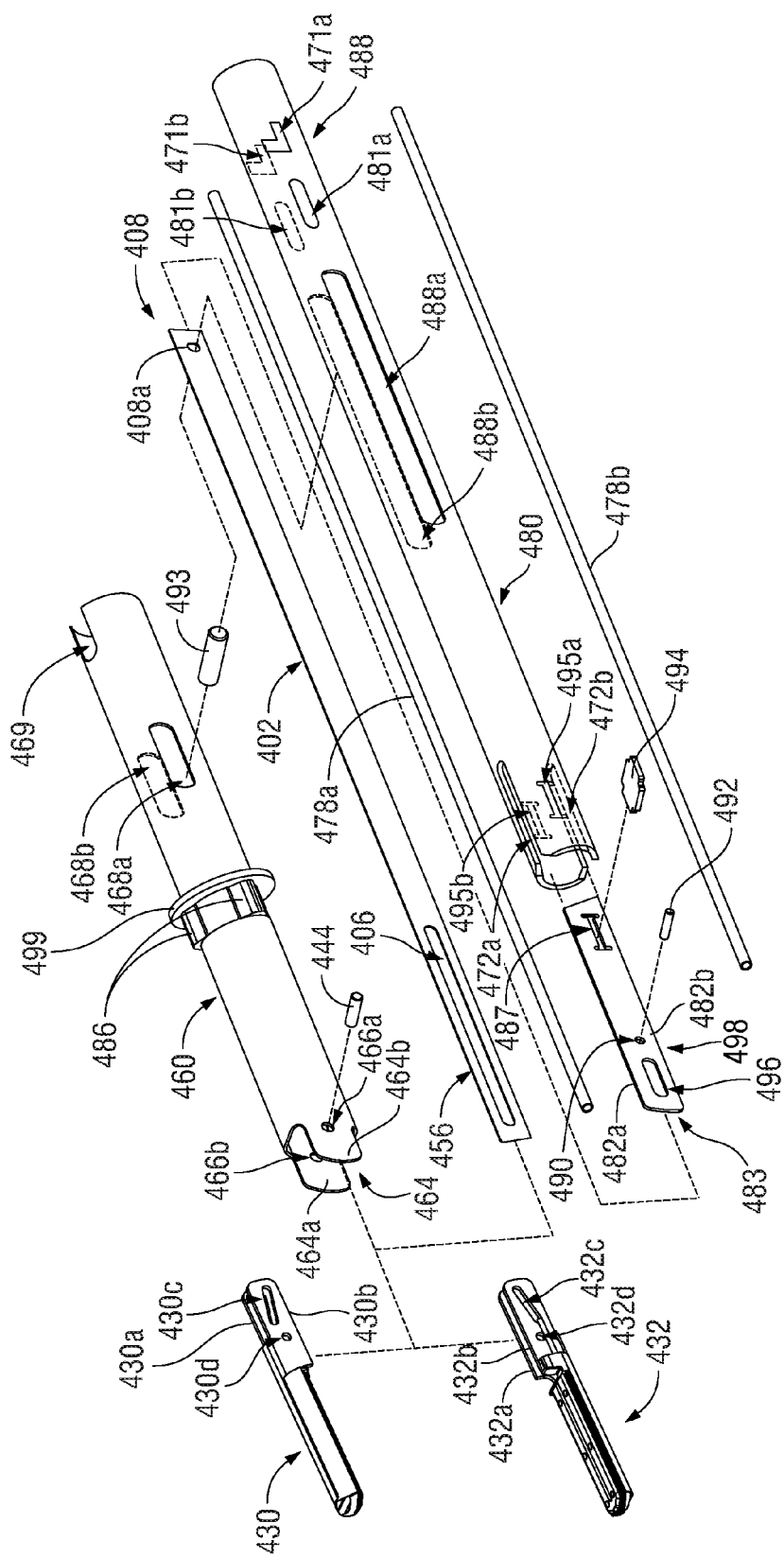
FIG. 3A is a perspective view of the end effector and elongated shaft of FIG. 1 with parts separated.

Referring now to FIG. 3A, the elongated shaft 416 includes various longitudinal components that operatively couple the end effector 414 to the various actuators supported by the housing 412 (FIG. 1). An outer shaft member 460 defines an exterior surface of the elongated shaft 416 and supports movement of other components therethrough as described below. The outer shaft member 460 may be constructed from a flat stock piece of metal. In constructing the outer shaft member 460, a stamping, punching or similar metal-working process may be employed to initially generate a flat blank that includes an appropriate outer profile and any interior openings or features. Thereafter, the necessary bends and curves may be formed by bending the flat blank with a press brake, or other suitable metal-working equipment. The outer shaft member 460 may be formed by folding the flat blank into a generally circular profile (or generally rectangular profile) such that two opposing longitudinal edges of the flat blank meet at a longitudinal seam (not explicitly shown). Although the longitudinal seam does not necessarily require joining by a mechanical interlock or any other suitable process, the seam may, in some embodiments, be joined by laser welding (or other suitable process) to form a continuous circular or other geometric (e.g., rectangular) profile. The seam may be generally straight, or alternatively, a box joint, a dovetail joint, or any other suitable interface known in the metal-working arts.

The outer shaft member 460 defines a clevis 464 at a distal end thereof for receiving the jaw members 430 and 432. Opposing vertical sidewalls 464a and 464b of the outer shaft member 460 include respective bores 466a, 466b extending therethrough to frictionally support the pivot pin 444 and maintain an orientation of the pivot pin 444 with respect to the outer shaft member 460. Alternatively or additionally, the pivot pin 444 may be fastened to the outer shaft member 460 by a laser or heat-based welding, adhesives, chemical bonding, or other suitable manufacturing processes.

At a proximal portion of the outer shaft member 460, various features are provided that serve to couple the outer shaft member 460 to various elements of the housing 412. More specifically, the proximal portion of the outer shaft member 460 includes, in order from distal to proximal, a series of tabs 486 extending therefrom, a washer 499 extending around outer shaft member 460, a pair of opposing longitudinal slots 468a, 468b defined therethrough and provided to allow longitudinal translation of a dowel pin 493 therethrough, and a longitudinal slot 469 extending distally from a proximal end thereof to couple the outer shaft member 460 to the rotation knob 428. The connection established between the outer shaft member 460 and the rotation knob 428 is described below with reference to FIG. 4. As shown in FIGS. 15A-15D, the series of tabs 486 and the washer 499 serve to aid in securing the proximal portion of the outer shaft member 460 within the housing 412.

The pivot pin 444 extends through a proximal portion of each of the jaw members 430, 432 to pivotally support the jaw members 430, 432 at the distal end of the outer shaft member 460. With reference to FIG. 8, a proximal portion of each of the jaw members 430, 432 is configured as a "double flag." The double flag configuration refers to the two laterally spaced parallel flanges or "flags" 430a, 430b and 432a, 432b respectively, extending proximally from a distal portion of the jaw members 430 and 432. A lateral cam slot 430c and a lateral pivot bore 430d extend through each of the flags 430a, 430b of the upper jaw member 430. Similarly, a lateral cam slot 432c and a lateral pivot bore 432d extend through each of the flags 432a, 432b of the lower jaw member 432. The pivot bores 430d, 432d receive the pivot pin 444 in a slip-fit relation that permits the jaw members 430, 432 to pivot about the pivot pin 444 to move the end effector 414 between the open and closed configurations (FIGS. 2A and 2B, respectively).

Figure 3B:
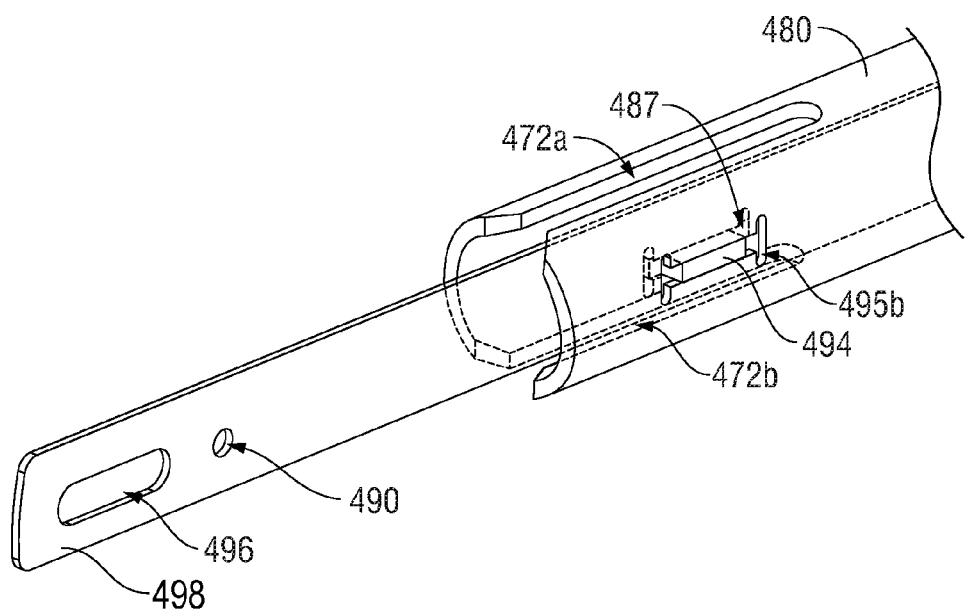
FIG. 3B is an enlarged perspective view of a distal portion of the electrosurgical forceps of FIG. 1 depicting a distal knife guide coupled to an inner shaft member.

An inner shaft member 480 is received within the outer shaft member 460 and is configured for longitudinal motion with respect to the outer shaft member 460. A distal knife guide 498 includes sidewalls 482a, 482b and a proximal key slot 487 that supports a key member 494 therethrough. During assembly of electrosurgical forceps 400, the distal knife guide 498 is slid proximally within a distal end of the inner shaft member 480, such that the inner shaft member 480 surrounds a portion of the distal knife guide 498, and opposing lateral sides of the key member 494 align with and fit within opposing longitudinal key slots 495a, 495b defined through the inner shaft member 480 to couple the knife guide 498 to the inner shaft member 480 (FIG. 3B). The inner shaft member 480 includes a pair of opposing longitudinal slots 472a, 472b extending proximally from a distal end of the inner shaft member 480 along a portion of the inner shaft member 480 between the opposing longitudinal key slots 495a, 495b. The longitudinal slots 472a, 472b allow the distal end of the inner shaft member 480 to aid in sliding of the distal knife guide 498 proximally within the inner shaft member 480. Once the key member 494 is aligned with and fit within the longitudinal key slots 495a, 495b, the key member 494 effectively couples the distal knife guide 498 to the inner shaft member 480, as depicted by FIG. 3B.

The sidewalls 482a, 482b define a longitudinal slot 483 through the distal knife guide 498 that provides lateral support to the knife 402. The knife 402 is substantially surrounded at a distal end thereof by the distal knife guide 498 on four lateral sides and the sidewalls 482a, 482b of the distal knife guide 498 constrain side-to-side lateral motion of the knife 402. Thus, the distal knife guide 498 serves to urge the knife 402 into a central position within the elongated shaft 416, thereby ensuring proper alignment of the knife 402 as the knife 402 reciprocates within knife channel 458 (FIG. 2A). The distal knife guide 498 includes features for operatively coupling the inner shaft member 480 to the end effector 414. A proximal portion 488 of the inner shaft member 480 is configured for receipt within the housing 412 (FIG. 1), and includes features for operatively coupling the inner shaft member 480 to the actuators supported thereon, e.g. the movable handle 422.

The distal knife guide 498 includes a through bore 490 extending through the sidewalls 482a, 482b for receiving the cam pin 492. Distally of the through bore 490, a longitudinal slot 496 is defined through the sidewalls 482a, 482b. The longitudinal slot 496 provides clearance for the pivot pin 444, and thus, permits longitudinal reciprocation of the inner shaft member 480 independent of the pivot pin 444.

The proximal portion 488 of the inner shaft member 480 includes, in order from distal to proximal, a pair of opposing longitudinal knife slots 488a, 488b extending therethrough, a pair of opposing distal locking slots 481a, 481b extending therethrough, a pair of opposing proximal locking slots 471a, 471b extending therethrough, and a proximal end 491 configured to engage a suitable mechanical interface within the housing 412 to aid in proper support of the inner shaft member 480 within the housing 412 (see FIGS. 12 and 15A-15D).

The knife 402 is a generally flat, metal component defining a profile that may be constructed by a stamping process. The knife 402 supports the sharpened knife blade 456 at a distal-most end thereof. The sharp edge of the knife blade 456 may be applied to the distal end of the knife 402 subsequent to the stamping process that forms the profile. For example, various manufacturing techniques may be employed such as grinding, coining, electrochemical etching, electropolishing, or other suitable manufacturing processes, for forming sharpened edges. A longitudinal slot 406 is defined within the knife 402 to provide clearance for the pivot pin 444, the cam pin 492, and the key member 494. A proximal through bore 408a extends through a proximal portion 408 of the knife 402 and provides a mechanism for operatively coupling the knife 402 to the trigger 426 via the dowel pin 493. The connection between the knife 402 and the trigger 426 is described in detail below with reference to FIGS. 12, 13, 14A, and 14B.

Figure 4:
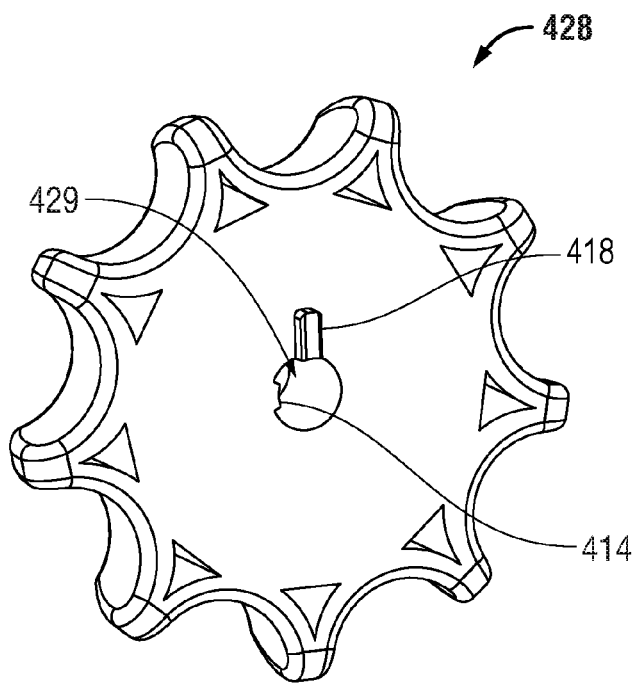
FIG. 4 is a proximally-facing perspective view of a rotation knob depicting a cavity for receiving the elongated shaft of FIG. 1.

Referring now to FIG. 4, the rotation knob 428 includes a passageway 429 defined therethrough for receiving the outer shaft member 460. The passageway 429 has a generally circular profile corresponding to the circular profile of the outer shaft member 460. The passageway 429 includes a longitudinal keying member 414 that is configured to align with and be seated within longitudinal slot 469 (FIG. 3A) of the outer shaft member 460. The keying member 414 projects laterally inward along the length of passageway 429 such that the insertion of the proximal end of the outer shaft member 460 into the passageway 429 of the rotation knob 428 operatively couples the outer shaft member 460 to the rotation knob 428 and, thus, permits longitudinal motion of the inner shaft member 480 therethrough.

In one embodiment, a cable clearance passageway (not shown) is defined through rotation knob 428 to permit passage of electrical cables or wires that electrically couple the sealing plates 448, 450 to the electrosurgical generator 443 (FIG. 1). Rotational motion imparted to the rotation knob 428 may thus impart rotational motion to each of the components of the elongated shaft 416, and to the end effector 414, which is coupled thereto.

Figure 13:
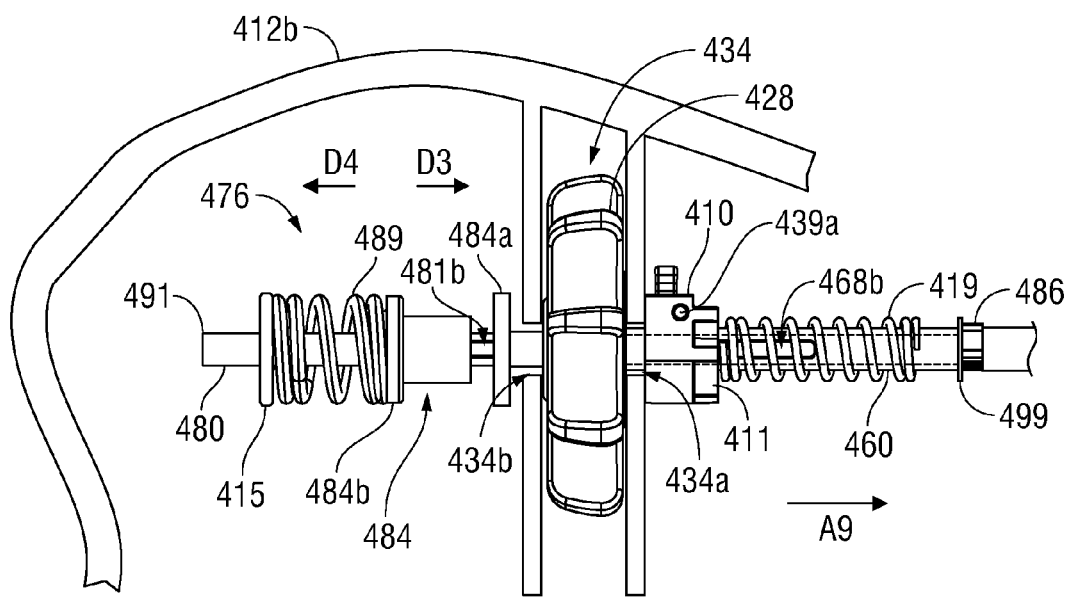
FIG. 13 is a partial, side view of a proximal portion of the jaw actuation mechanism of FIG. 6 depicting a connection between the jaw actuation mechanism and the jaw drive rod mechanism for imparting longitudinal movement to the jaw drive rod.

As shown in FIG. 13, the rotation knob 428 is seated within an interior compartment 434 of the housing 412 and, as shown in FIG. 1, extends laterally outward from opposing sides of the housing 412 (only shown extending laterally outward from housing half 412b). The interior compartment 434 defines distal and proximal passageways 434a and 434b that permit the passage of the components of the elongated shaft 416 therethrough. The rotational motion of the rotation knob 428 may be limited by a stop boss 418 projecting distally from the rotation knob 428 (FIG. 4). The stop boss 418 is positioned to engage the distal passage 434a of the compartment 434 to restrict rotational motion of the rotation knob 428. For example, in some embodiments, the stop boss 418 may engage the distal passage 434a to restrict rotational motion of the rotation knob 428 to 180 degrees in either direction.

Figure 5:
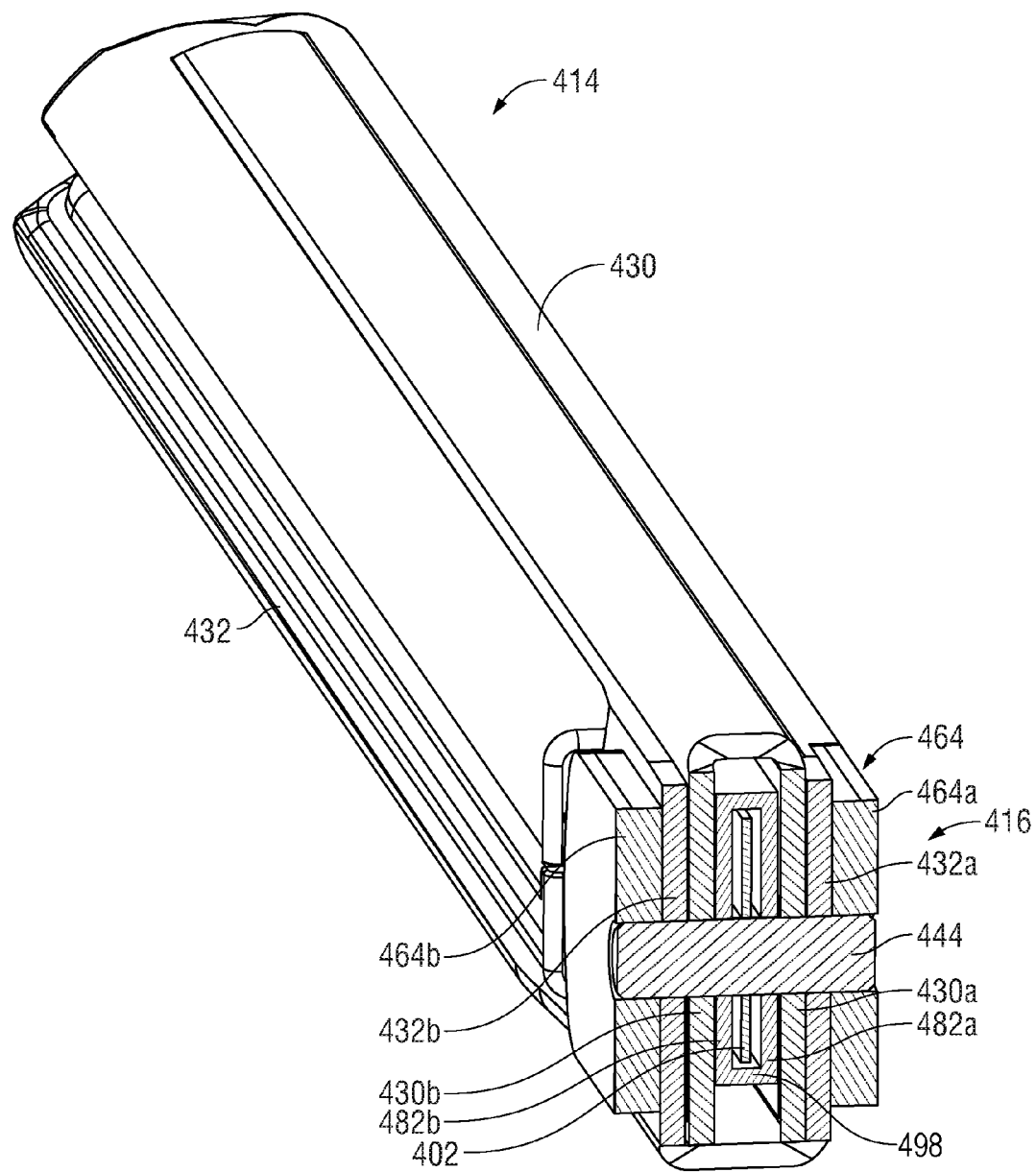
FIG. 5 is a cross-sectional, perspective view of the end effector assembled with the elongated shaft of FIG. 1.

Referring now to FIG. 5, the end effector 414 is coupled to the distal end of the elongated shaft 416 by the pivot pin 444. The pivot pin 444 is coupled to the sidewalls 464a and 464b of the clevis 464 defined at the distal end of the outer shaft member 460. Thus, the pivot pin 444 represents a longitudinally stationary reference for the longitudinal movements of inner shaft member 480 and the knife 402. Laterally inward of the sidewalls 464a, 464b, the pivot pin 444 extends through the flags 432a, 432b of the lower jaw member 432, the flags 430a and 430b of the upper jaw member 430, the sidewalls 482a, 482b of the knife guide 498, and the knife 402. The jaw members 430, 432 are free to pivot about the pivot pin 444, and the inner shaft member 480 and the knife 402 are free to translate longitudinally around the pivot pin 444.

Figure 6:
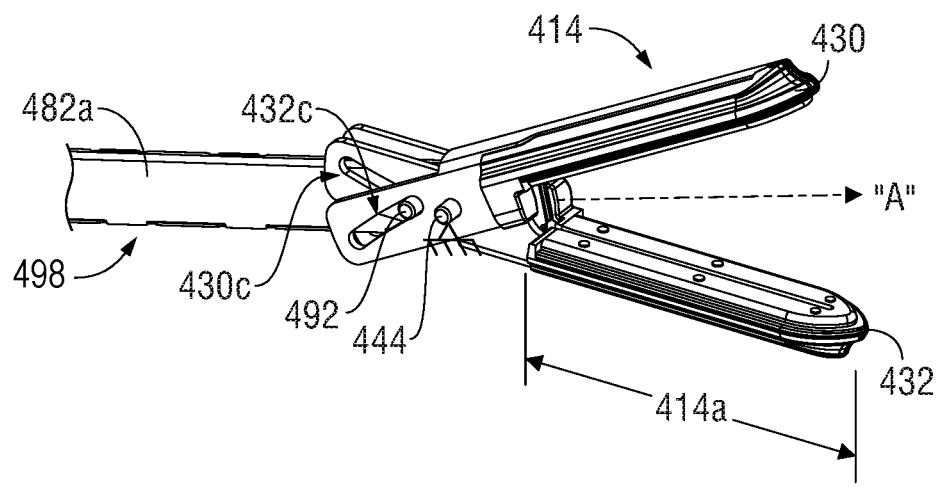
FIG. 6 is a partial, perspective view of a distal portion of a jaw actuation mechanism of the end effector of FIG. 1.

Referring now to FIG. 6, the end effector 414 is shown in the open configuration. Since the knife guide 498 is coupled to the cam pin 492, when the inner shaft member 480 is in the distal position, the cam pin 492 is located in a distal position in cam slots 430c and 432c defined through the flags 430a, 430b, 432a, 432b of the jaw members 430, 432, respectively.

The inner shaft member 480 may be drawn proximally relative to the pivot pin 444 to move the end effector 414 to the closed configuration (see FIG. 2B). Since the longitudinal position of the pivot pin 444 is fixed (by the outer shaft member 460, which is removed from view in FIG. 6 for clarity), and since the cam slots 430c, 432c are obliquely arranged with respect to the longitudinal axis A-A, proximal retraction of the cam pin 492 through the cam slots 430c, 432c induces the jaw members 430, 432 to pivot toward one another about the pivot pin 444. Conversely, when the end effector 414 is in the closed configuration, longitudinal translation of the inner shaft member 480 in a distal direction induces the jaw members 430, 432 to pivot away from one another toward the open configuration.

Figure 7:
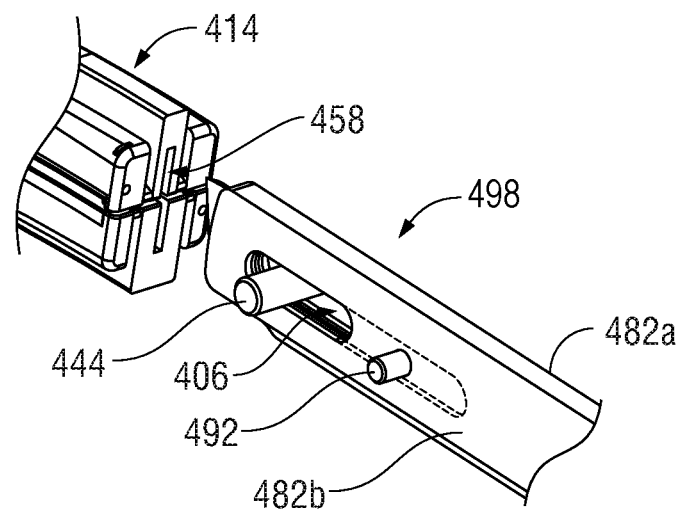
FIG. 7 is a partial, perspective view of distal portion of a knife actuation mechanism of the end effector of FIG. 1.

Referring now to FIG. 7, the longitudinal slot 406 in the knife 402 extends around both the pivot pin 444 and the cam pin 492, and thus the pins 444, 492 do not interfere with the reciprocal motion of the knife 402. The pivot pin 444 and cam pin 492 extend through the slot 406 in such a manner as to guide longitudinal motion of the knife 402 as well as constrain vertical motion of the knife 402. The blade 456 at the distal-most end of the knife 402 is centrally aligned by the knife guide 498, as discussed hereinabove. Properly aligned, the blade 456 readily enters the knife channel 458 defined in the jaw members 430, 432.

Referring now to FIGS. 8 and 9, the lower jaw member 432 is constructed of three major components. These components include a double-flag jaw insert 440, an insulator 442 and the sealing plate 448. The flags 432a, 432b of the jaw member 432 define a proximal portion of the double-flag jaw insert 440, and a generally u-shaped channel 444 extends distally to support the tissue engaging portion of the jaw member 432. The double-flag jaw insert 440 includes various planar surfaces, and may be constructed as a sheet metal component formed by a stamping process. In such a stamping process, the cam slots 432c and pivot holes 432d may be punched into a flat blank, and subsequently the blank may be bent to form the flags 432a, 432b and the u-shaped channel 444.

The insulator 442 may be constructed of an electrically insulative plastic such as a polyphthalamide (PPA) (e.g., Amodel®), polycarbonate (PC), acrylonitrile butadiene styrene (ABS), a blend of PC and ABS, nylon, ceramic, etc. The electrically insulative plastic may be overmolded onto the jaw insert 440 in a single-shot injection molding process such that sealing plate 448 is overmolded to the jaw insert 440. Additionally or alternatively, the electrically insulative plastic may be mechanically coupled to the jaw insert 440, e.g., pressed, snapped, glued, etc. Various features may be molded into the insulator 442 that facilitate the attachment of the sealing plate 448 to the insert 440. For example, tabs may be provided that permit a snap-fit attachment of the sealing plate 448, or ridges may formed that permit ultrasonic welding of the sealing plate 448 onto the insulator 442. The sealing plate 448 may be constructed of an electrically conductive metal, and may be stamped from a flat sheet stock.

Referring now to FIG. 10, the flags 430a, 430b of the upper jaw member 430 are depicted schematically in a nestled configuration with respect to the flags 432a, 432b of the lower jaw member 432. The proximal portion of the upper jaw member 430 is narrower than the proximal portion of the lower jaw member 432, and thus, a lateral spacing "S" between the flags 432a, 432b is sufficient to permit the flags 430a and 430b to be positioned therebetween. A pivot axis "$P_O$" extends through an overlapping portion of the flags 430a, 432a, and 430b, 432a such that the upper and lower jaw members 430, 432 may pivot about the common axis "$P_O$." In the nestled configuration, the proximal portions of the upper and lower jaw members 430, 432 also share a common centerline "CL-1" that is transverse with respect to the pivot axis "$P_O$."

An alternative to the nestled configuration illustrated in FIG. 10 is the offset configuration illustrated schematically in FIG. 11. A proximal portion of double-flag upper jaw member 450 includes flags 450a and 450b. A proximal portion of a double-flag lower jaw member 452 includes flags 452a and 452b and exhibits a width that is identical to a width of the proximal portion of the upper jaw member 450. To provide an overlapping portion of the flags 450a, 452a and 450b, 452b such that the jaw members 450, 452 may pivot about the common axis "$P_0$," one flag 450a of the upper jaw member 450 is positioned on a laterally exterior side of the corresponding flag 452a of the lower jaw member 452, and the other flag 450b of the upper jaw member 450 is positioned on a laterally interior side of the corresponding flag 452b of the lower jaw member 452. In the offset configuration, a centerline "CL-2" of the proximal portion of the upper jaw member 450 is laterally offset with respect to a centerline "CL-3" of the lower jaw member 452.

Figure 12:
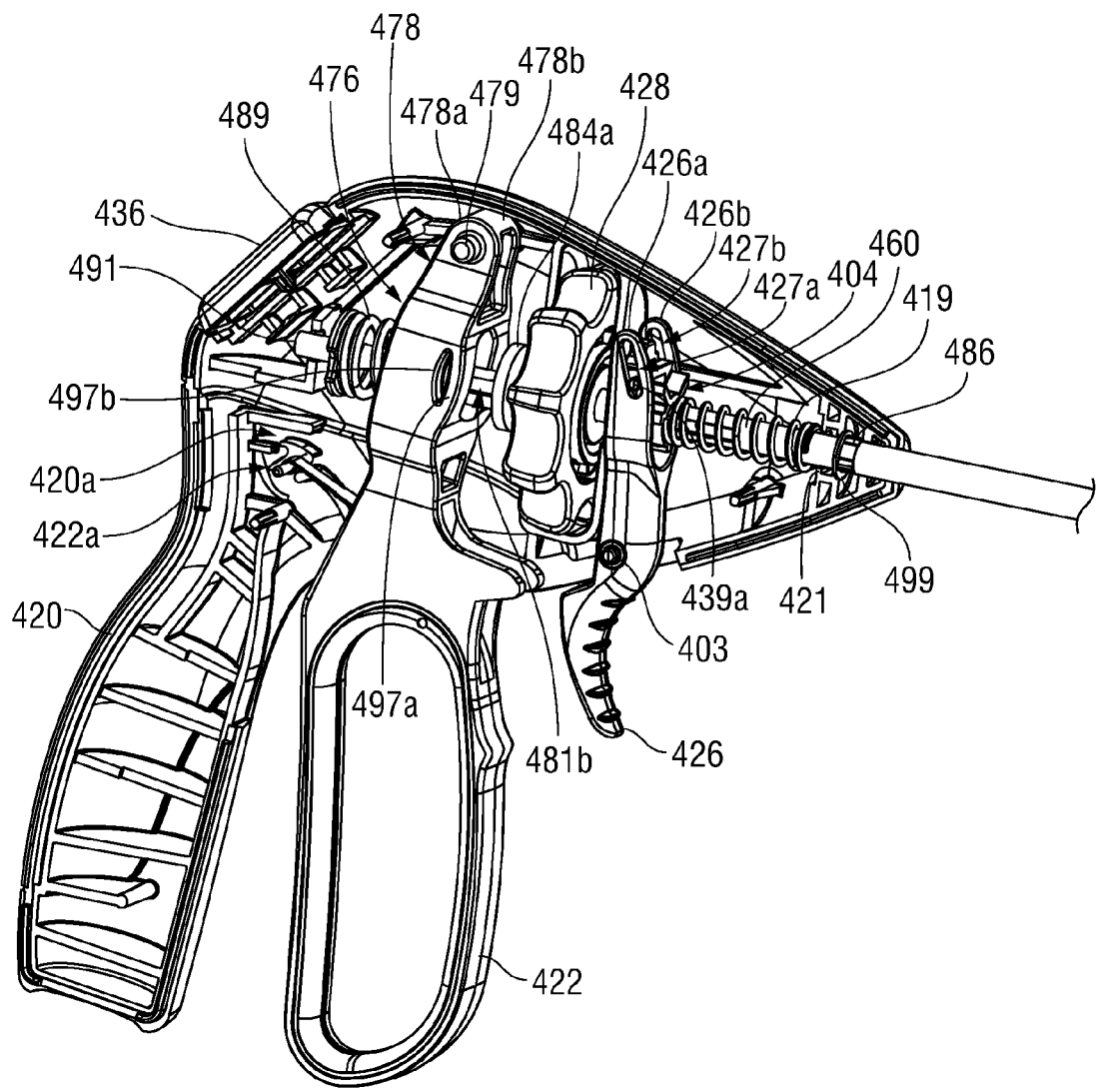
FIG. 12 is a perspective view of a proximal portion of the instrument of FIG. 1 with a portion of the housing removed revealing internal components.

Referring now to FIG. 12, the connection of the movable handle 422 and the knife trigger 426 to the longitudinally movable components of the elongated shaft 416 is described. The movable handle 422 may be manipulated to impart longitudinal motion to the inner shaft member 480, and the knife trigger 426 may be manipulated to impart longitudinal motion to the knife 402. As discussed above, longitudinal motion of the inner shaft member 480 serves to move the end effector 414 between the open configuration of FIG. 2A and the closed configuration of FIG. 2B, and longitudinal motion of the knife 402 serves to move knife blade 456 through knife channel 458 (FIG. 2A).

The movable handle 422 is operatively coupled to the inner shaft member 480 by a connection mechanism 476 (FIG. 12). The connection mechanism 476 includes a clevis 478 defined at an upper end of the movable handle 422. The clevis 478 is pivotally supported on the left housing half 412b by a pivot boss 479. A second complementary pivot boss (not shown) is provided on the right housing half 412a to support the clevis 478. Each of two upper flanges 478a and 478b of the clevis 478 extend upwardly about opposing sides of a drive collar 484 supported on the inner shaft member 480 and include rounded drive surfaces 497a and 497b thereon. Drive surface 497a engages a proximal-facing surface of a distal lock collar 484a and drive surface 497b engages a distal facing surface of a proximal rim 484b of the drive collar 484 (FIG. 13). The distal lock collar 484a engages the opposing distal locking slots 481a, 481b (FIG. 3A) extending through the proximal portion 488 of the inner shaft member 480 to lock-fit the distal lock collar 484a to the inner shaft member 480. Thus, the distal lock collar 484a is prevented from longitudinal motion relative to the inner shaft member 480. Drive surface 497a is arranged along the longitudinal axis A-A such that pivotal motions of the movable handle 422 about the pivot bosses 479 induce corresponding longitudinal motion of the drive collar 484 along the longitudinal axis A-A in the proximal direction. Drive surface 497b is arranged along the longitudinal axis A-A such that pivotal motions of the movable handle 422 about the pivot bosses 479 induce corresponding longitudinal motion of the distal lock collar 484a along the longitudinal axis A-A in the distal direction.

Referring now to FIG. 13, proximal longitudinal motion may be imparted to the inner shaft member 480 by pushing the proximal rim 484b of the drive collar 484 proximally with the movable handle 422 (FIG. 12) as indicated by arrow D4. The proximal rim 484b engages a spring 489 that is constrained between the proximal rim 484b and a proximal lock collar 415. The proximal lock collar 415 engages the opposing proximal locking slots 471a, 471b (FIG. 3A) extending through the proximal portion 488 of the inner shaft member 480 to lock-fit the proximal lock collar 415 to the inner shaft member 480. Thus, the proximal lock collar 415 is prevented from longitudinal motion relative to the inner shaft member 480 and serves as a proximal stop against which spring 489 compresses.

Distal longitudinal motion is imparted to the inner shaft member 480 by pushing the distal lock collar 484a distally with drive surface 497a of movable handle 422 as indicated by arrow D3 (FIG. 13). Distal longitudinal motion of the distal lock collar 484a induces a corresponding distal motion of the inner shaft member 480 by virtue of the lock-fit coupling of the distal lock collar 484a to the opposing proximal locking slots 471a, 471b extending through the proximal portion 488 of the inner shaft member 480 (FIG. 3A).

Proximal longitudinal motion of the inner shaft member 480 draws the cam pin 492 proximally to pivot the jaw members 430, 432 toward one another to move the end effector 414 to the closed configuration as described above with reference to FIG. 6. Once the jaw members 430 and 432 are closed, the inner shaft member 480 essentially bottoms out (i.e., further proximal movement of the inner shaft member 480 is prohibited since the jaw members 430, 432 contact one another). Further proximal movement of the movable handle 422 (FIG. 12), however, will continue to move the drive collar 484 proximally. This continued proximal movement of the drive collar 484 further compresses the spring 489 to impart additional force to the inner shaft member 480, which results in additional closure force applied to tissue grasped between the jaw members 430, 432 (see FIG. 2B). The spring 489 also serves to bias the movable handle 422 to an open configuration such that the movable handle 422 is separated from the stationary handle 420.

Referring again to FIG. 12, the trigger 426 is pivotally supported in the housing 412 about a pivot boss 403 protruding from the trigger 426. The trigger 426 is operatively coupled to the knife 402 by a knife connection mechanism 404 such that pivotal motion of the trigger 426 induces longitudinal motion of the knife 402. The knife connection mechanism 404 includes upper flanges 426a, 426b of the trigger 426 and a knife collar 410.

Referring now to FIGS. 13, 14A, and 14B, the knife collar 410 includes a cap member 411 coupled thereto and a pair of integrally formed pin bosses 439a, 439b extending from opposing sides thereof. The knife collar 410 may include indentations or catches defined therein (not shown) that receive corresponding snap-in features (e.g., arms) of the cap member 411. The cap 411 may thus be assembled to the knife collar 410 such that the cap 411 and the knife collar 410 translate together. As shown by FIG. 14B, the coupling of the knife collar 410 to the cap 411 forms an interior circular channel 413 to capture the dowel pin 493 therein such that the dowel pin 493 is supported on opposing ends between the knife collar 410 and the cap 411. The dowel pin 493 extends through the proximal through bore 408a extending through a proximal portion 408 of the knife 402 (FIG. 3A) to operably couple the knife 402 to the knife collar 410. Upon longitudinal motion of the inner shaft member 480, dowel pin 493 translates longitudinally within knife slots 488a, 488b, respectively, of the inner shaft member 480 such that the longitudinal motion of inner shaft member 480 is unimpeded by dowel pin 493. Upon rotation of the elongated shaft 416 and end effector 414 about the longitudinal axis A-A via the rotation knob 428 (FIG. 1), dowel pin 493 freely rotates within the interior circular channel 413 such that the outer and inner shaft members 460 and 480 (removed from view in FIG. 14B for clarity), the knife 402, and the dowel pin 493 rotate within the knife collar 410 about the longitudinal axis A-A. In this way, the knife collar 410 serves as a stationary reference for the rotational movement of the outer shaft member 460, the inner shaft member 480, the knife 402, and the dowel pin 493.

Referring again to FIG. 12, the upper flanges 426a, 426b of the trigger 426 include respective slots 427a, 427b defined therethrough that are configured to receive the pin bosses 439a, 439b, respectively, of the knife collar 410 such that pivotal motion of the trigger 426 induces longitudinal motion of the knife collar 410 and, thus, the knife 402 by virtue of the coupling of knife 402 to the knife collar 410 via the dowel pin 493 extending through the through bore 408a. During longitudinal motion of the knife collar 410, dowel pin 493 translates longitudinally within the opposing slots 468a, 468b of the outer shaft member 460 and the slots 488a, 488b of the inner shaft member 480.

Referring now to FIGS. 13 and 14A, when the trigger 426 is moved to induce motion of the knife collar 410 in order to translate the blade 456 through the knife channel 458, the knife collar 410 translates along the outer shaft member 460 in the direction of arrow A9 to abut a spring 419 such that spring 419 compresses against a distal portion 421 of the interior of the housing 412 (FIG. 12). The spring 419 biases the knife collar 410 in a proximal direction to a proximal position along the outer shaft member 460.

Figure 15A:
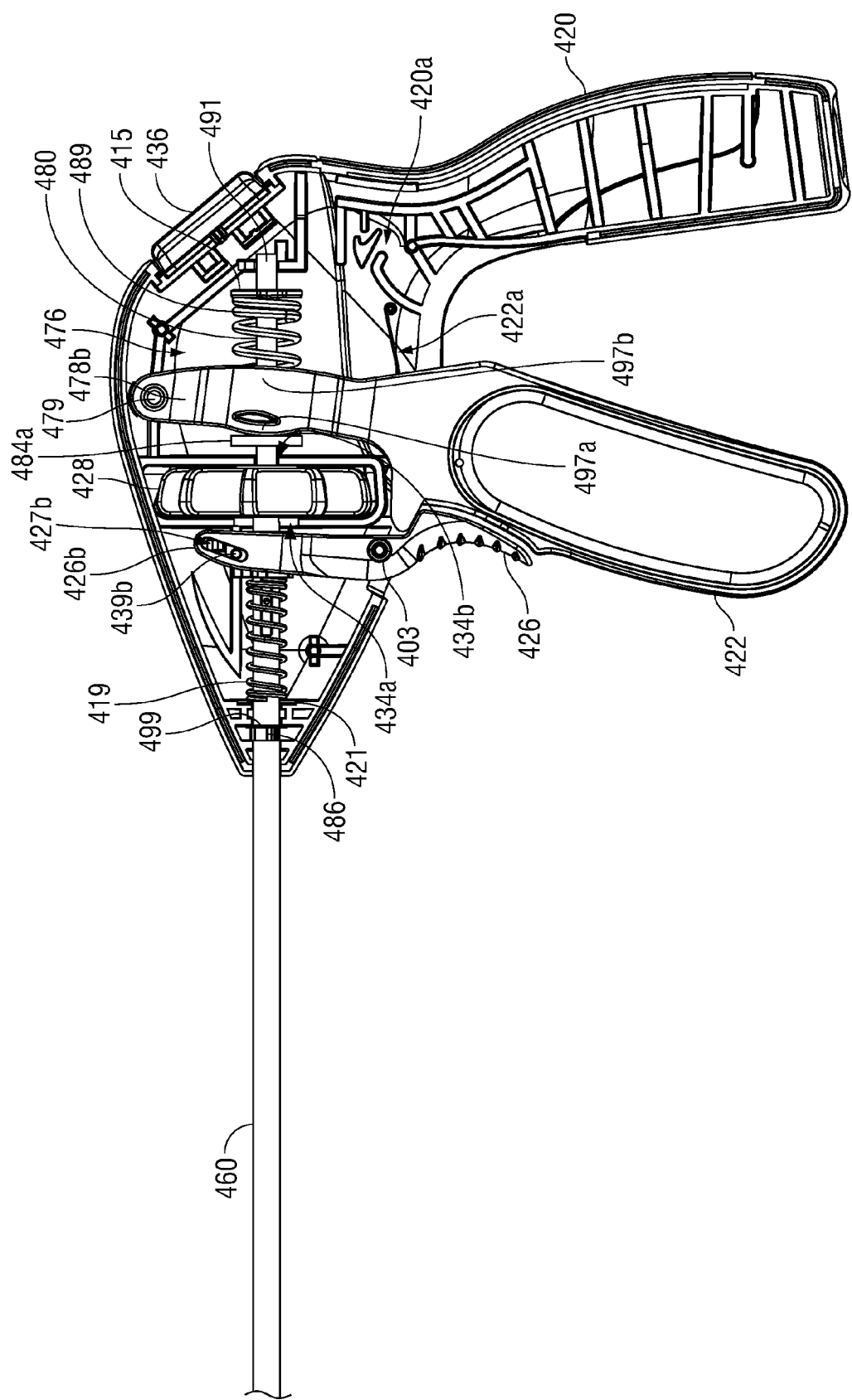
FIG. 15A is a side view of the proximal portion of the instrument of FIG. 12 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members.

Referring now to FIGS. 15A, 15B, 15C and 15D, a sequence of motions may be initiated by moving the movable handle 422 to induce motion of the jaw drive mechanism in order to close the jaws 430, 432, and by moving the trigger 426 to induce motion of the knife collar 410 in order to translate the blade 456 through the knife channel 458. Initially, both the moveable handle 422 and the knife trigger 426 are in a distal or un-actuated position as depicted in FIG. 15A. This arrangement of the moveable handle 422 and trigger 426 sustains the end effector 414 in the open configuration (FIG. 2A) wherein the jaw members 430, 432 are substantially spaced from one another, and the knife blade 456 is in a retracted or proximal position with respect to the jaw members 430, 432. The initial distal position of the trigger 422 is actively maintained by the influence of the spring 419 on the knife collar 410. The distal position of the moveable handle 422, however, is only passively maintained, e.g., by internal friction within the jaw actuation mechanism. When both the moveable handle 422 and the knife trigger 426 are in the distal, un-actuated position, pivotal motion of the knife trigger 426 in a proximal direction, i.e., toward the stationary handle 420, is prohibited by interference between the trigger 426 and moveable handle 422. This interference prohibits advancement of the knife blade through the knife channel 458 when the end effector 414 is in the open configuration.

Figure 15B:
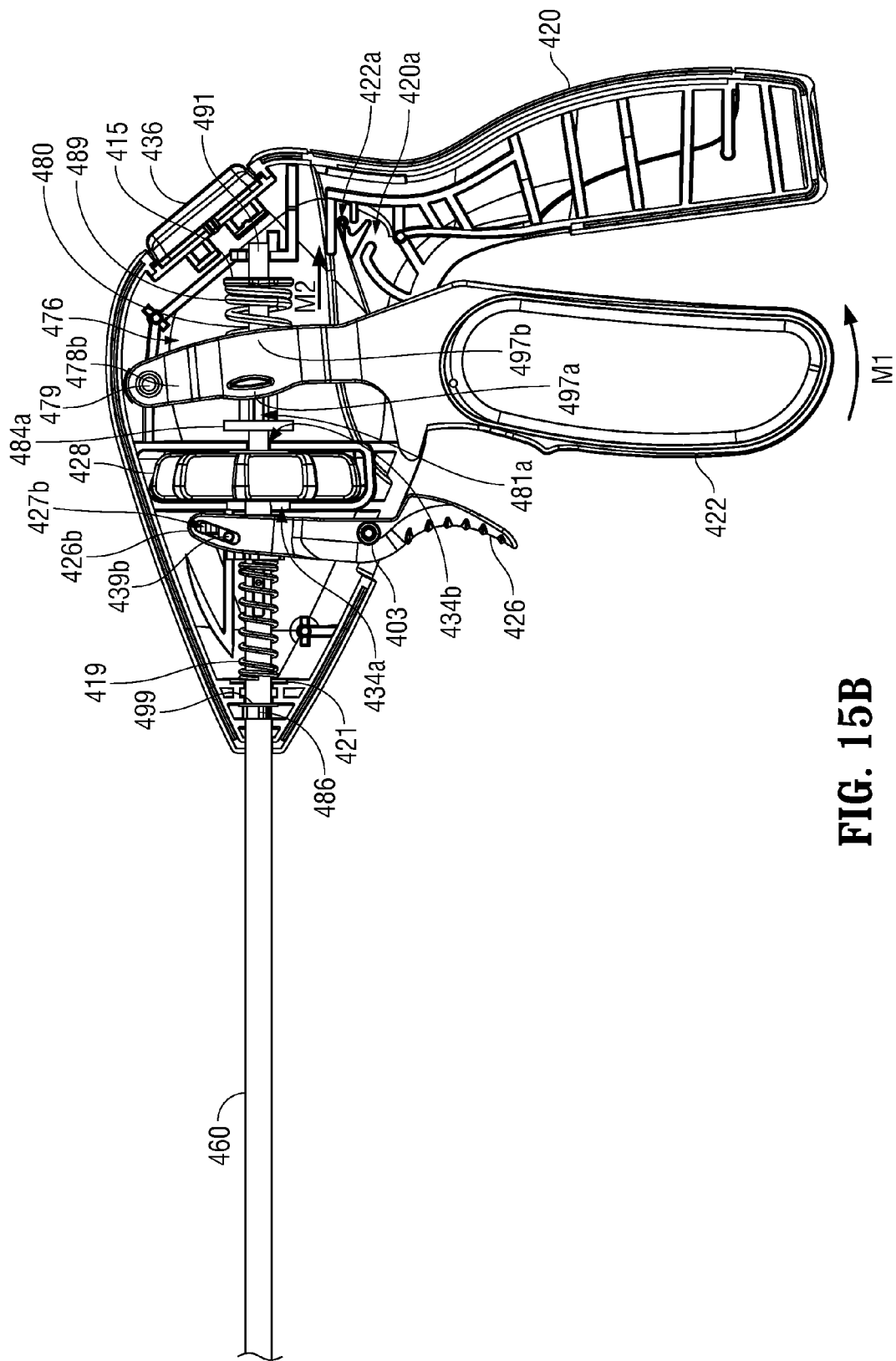
FIG. 15B is a side view of the proximal portion of the instrument of FIG. 12 depicting the movable handle in an intermediate position with respect to the stationary handle, which corresponds to a first closed configuration of the end effector wherein the jaw members encounter one another.

The movable handle 422 may be moved from the distal position of FIG. 15A to the intermediate position depicted in FIG. 15B to move the jaw members 430, 432 to the closed configuration (FIG. 2B). As the movable handle 422 pivots about the pivot boss 479 in the direction of arrow M1 (FIG. 15B), the drive surface 497b of the movable handle 422 engages the proximal rim 484b of the drive collar 484. The drive collar 484 and the spring 489 are both driven proximally against the proximal lock collar 415 and, thus, the inner shaft member 480 is driven proximally in the direction of arrow M2 (FIG. 15B). As discussed above with reference to FIG. 6, proximal movement of the inner shaft member 480 serves to draw the cam pin 492 proximally though the cam slots 430c, 432c of the jaw members 430, 432, respectively, and thus pivot the jaw members 430, 432 toward one another. As the jaw members 430, 432 engage one another and no further pivotal movement of the jaw members 430, 432 may be achieved, the jaw actuation mechanism "bottoms out" and further proximal movement of the cam pin 492 and the inner shaft member 480 is prevented.

Figure 15C:
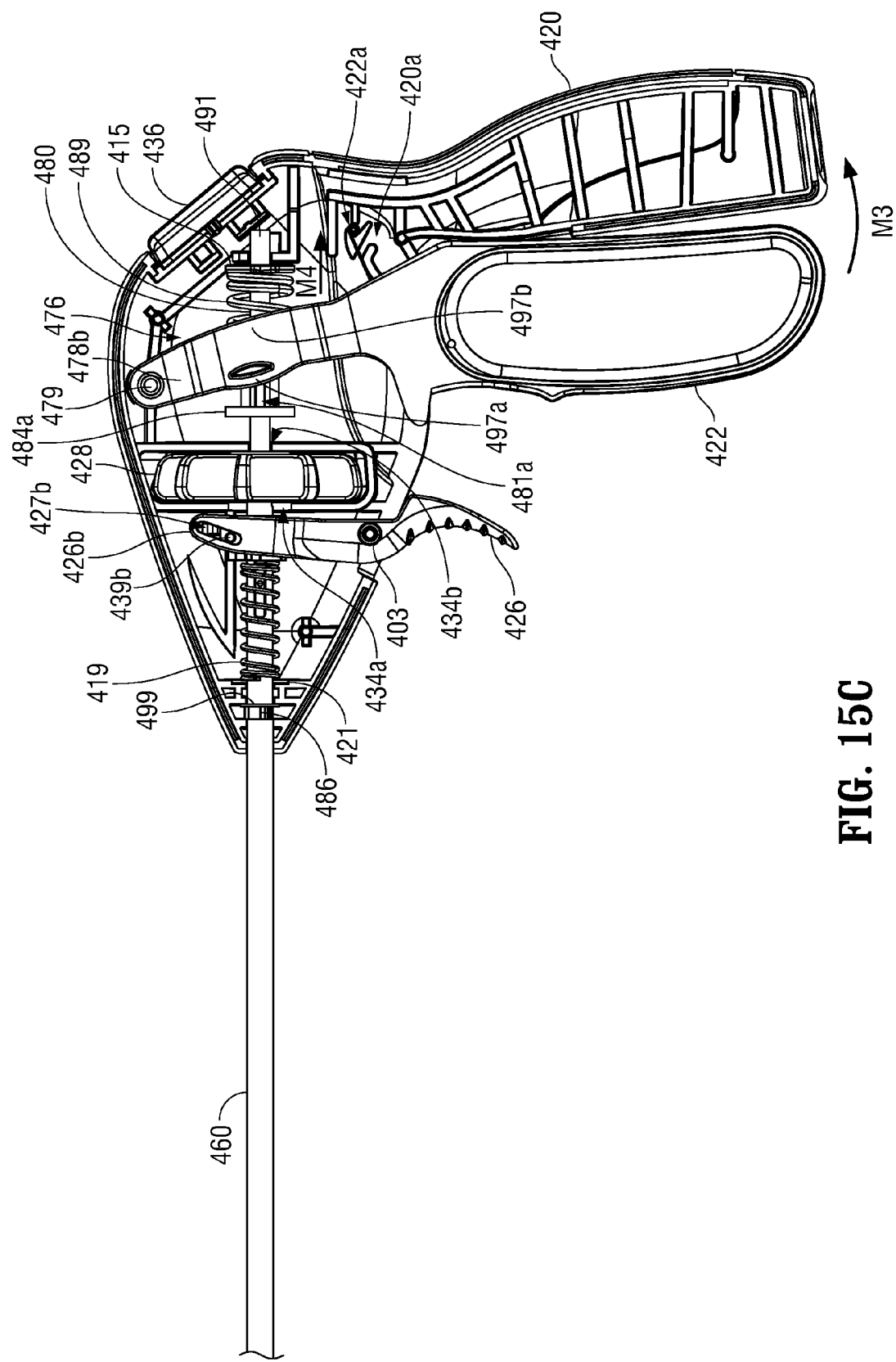
FIG. 15C is a side view of the proximal portion of the instrument of FIG. 12 depicting the movable handle in an approximated configuration with respect to the stationary handle, which corresponds to a second closed configuration of the end effector wherein the jaw members apply an appropriate pressure to generate a tissue seal.

The movable handle 422 may be moved from the intermediate position of FIG. 15B to the actuated or proximal position of FIG. 15C to increase the pressure applied by the jaw members 430, 432. As the movable handle 422 pivots further about the pivot boss 479 in the direction of arrow M3 (FIG. 15C), the drive surface 497b presses the proximal rim 484b of the drive collar 484 further distally against the spring 489 in the direction of arrow M4 (FIG. 15C). The spring 489 is compressed against the proximal lock collar 415, and a tensile force is transmitted through the inner shaft member 480 to the jaw members 430, 432. The tensile force supplied by the spring 489 ensures that the jaw members 430, 432 apply an appropriate pressure to effect a tissue seal. When the movable handle 422 is in the actuated or proximal position, electrosurgical energy may be selectively supplied to the end effector 414 to generate a tissue seal.

When the movable handle 422 is in the actuated or proximal position, a t-shaped latch 422a extending proximally from an upper portion of the moveable handle 422 is received in a railway 420a supported within the stationary handle 420. The railway 420a serves to temporarily lock the movable handle 422 in the proximal position against the bias of the spring 489. Thus, the railway 420a permits the maintenance of pressure at the end effector 414 without actively maintaining pressure on the movable handle 422. The flange 422a may be released from the railway 420a by pivoting the movable handle 422 proximally and releasing the movable handle 422 to move under the influence of the spring 489. Operation of the railway 420a is described in greater detail in U.S. patent application Ser. No. 11/595,194 to Hixson et al., now U.S. Pat. No. 7,766,910. In some embodiments (not shown), the latch 422a and the railway 420a may be eliminated to provide an instrument without the temporary locking capability provided by these features.

Figure 15D:
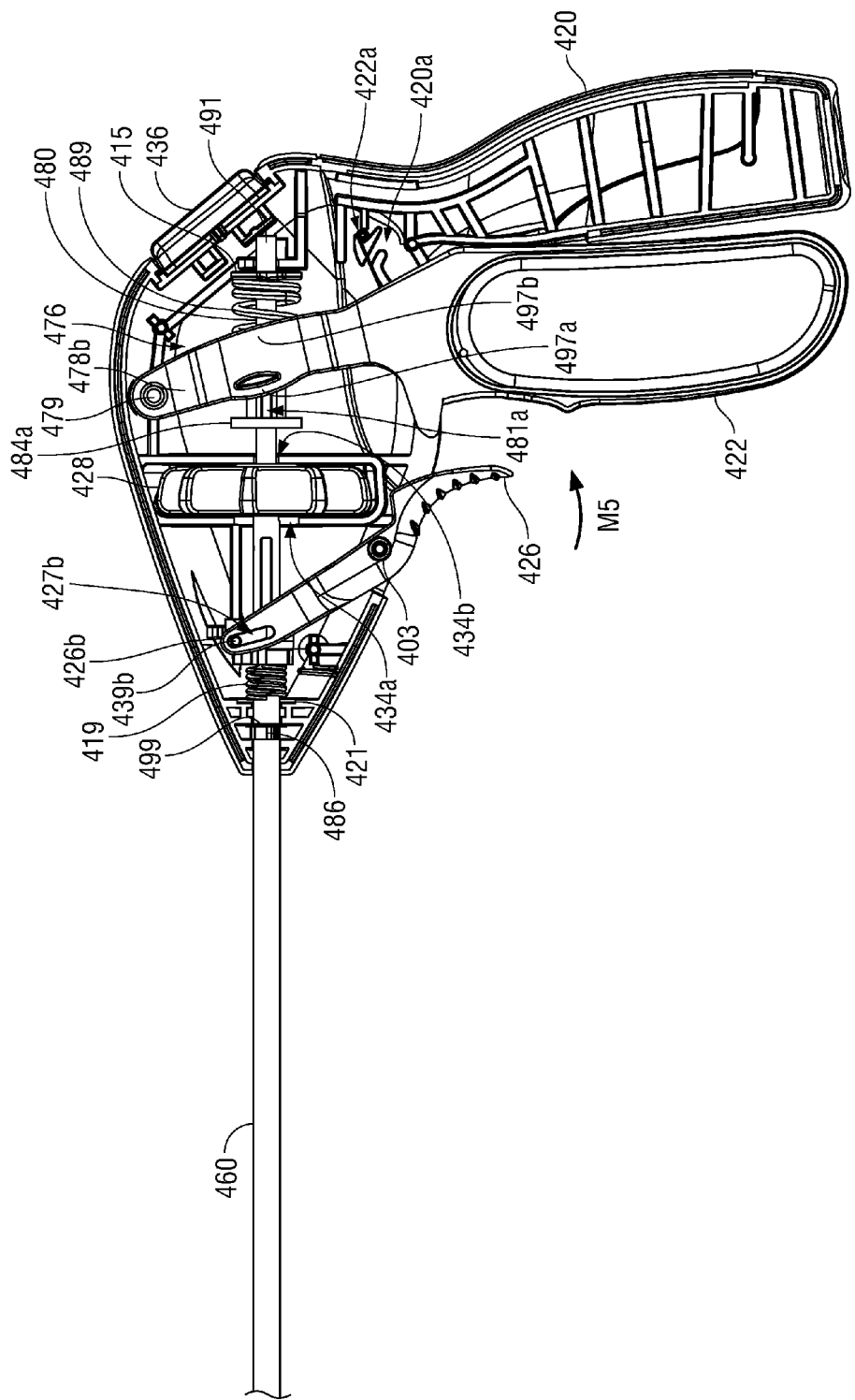
FIG. 15D is a side view of the proximal portion of the instrument of FIG. 12 depicting the knife trigger in an actuated configuration, which corresponds to an actuated or distal position of the knife with respect to the jaw members.

When the movable handle 422 is in the actuated or proximal position, the knife trigger 426 may be selectively moved from the distal position of FIG. 15C to the proximal position of FIG. 15D to advance the knife blade 456 distally through knife channel 458. The knife trigger 426 may be pivoted in the direction of arrow M5 (FIG. 15D), about pivot boss 403 to advance the flange 426b of the knife trigger 426 distally in the direction of arrow M6 such that the pin boss 439b translates within slot 427b from the position shown in FIGS. 15A-15C to the position shown in FIG. 15D. Although not explicitly shown in FIGS. 15A-15D, pin boss 439a translates within slot 427a in the same manner as described above with respect to pin boss 439b and slot 427b. Movement of flanges 426a, 426b draws the knife collar 410 distally, which induces distal longitudinal motion of the knife 402 by virtue of the coupling of knife 402 to the knife collar 410 via the dowel pin 493 extending through the through bore 408a, as described above with reference to FIGS. 3A and 14B.

An alternate embodiment of a connection mechanism for a surgical instrument, e.g., an alternate embodiment of an actuation mechanism such as the connection mechanism 476 described above with respect to FIGS. 12-15D is now described with respect to FIGS. 16-25. Wherever possible, like component numbering is utilized to identify like components.

It should be noted that although this description relates to a connection mechanism for a surgical instrument that includes an end effector assembly with jaw members such as surgical instrument 400 described above with respect to FIGS. 1-15D, the connection mechanism described herein may also be applied to other types of surgical instrumentation.

Figure 16:
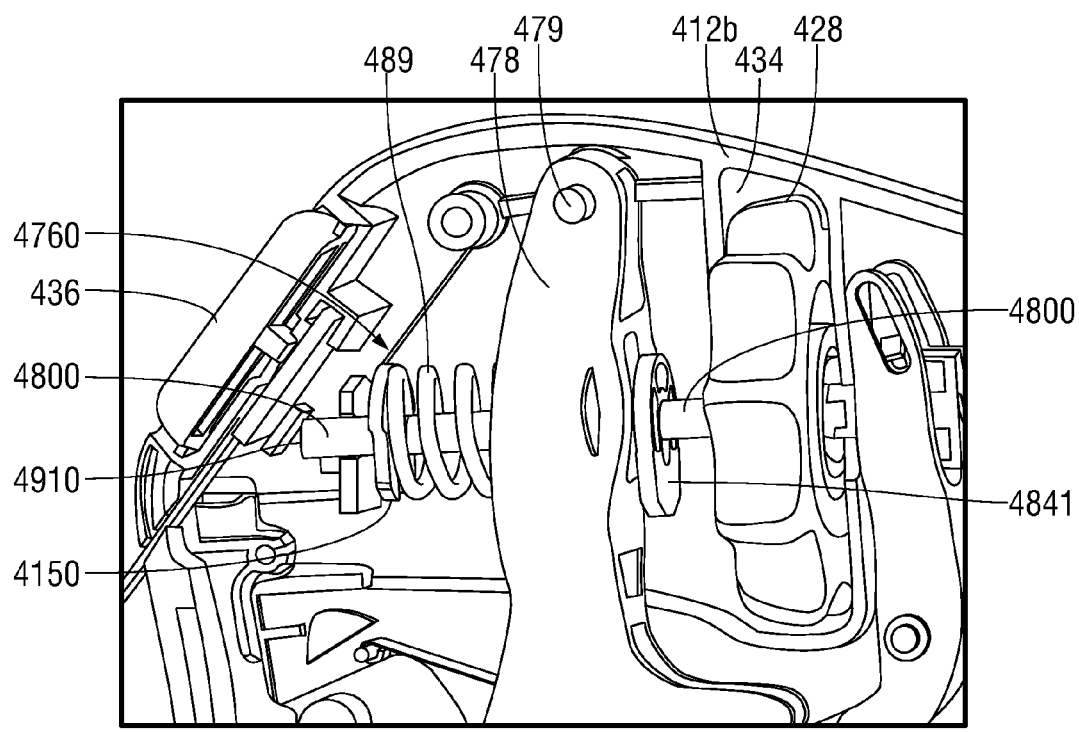
FIG. 16 is a partial, side view of a proximal portion of an alternate embodiment of a connection mechanism such as the jaw actuation mechanism of FIG. 13 depicting a connection between the jaw actuation mechanism and the jaw drive rod mechanism for imparting longitudinal movement to the jaw drive rod in a manner to enhance the delivery of a required shaft force such as to the jaw members illustrated in FIG. 6.

More particularly, FIG. 16 is a view of a proximal portion of an alternate embodiment of a connection mechanism for a surgical instrument (e.g., for surgical instrument 400 and elongated shaft member 416 described above with respect to FIGS. 1-15D) such as the jaw actuation mechanism of FIG. 13. FIG. 16 depicts connection mechanism 4760 between the jaw actuation mechanism and the jaw drive rod mechanism for imparting longitudinal movement to the jaw drive rod in a manner to enhance the delivery of a required shaft force such as to the pair of opposed jaw members 430, 432 illustrated in FIG. 6 via the elongated shaft 416 illustrated, for example, in FIGS. 1, 2A and 2B.

Figure 17:
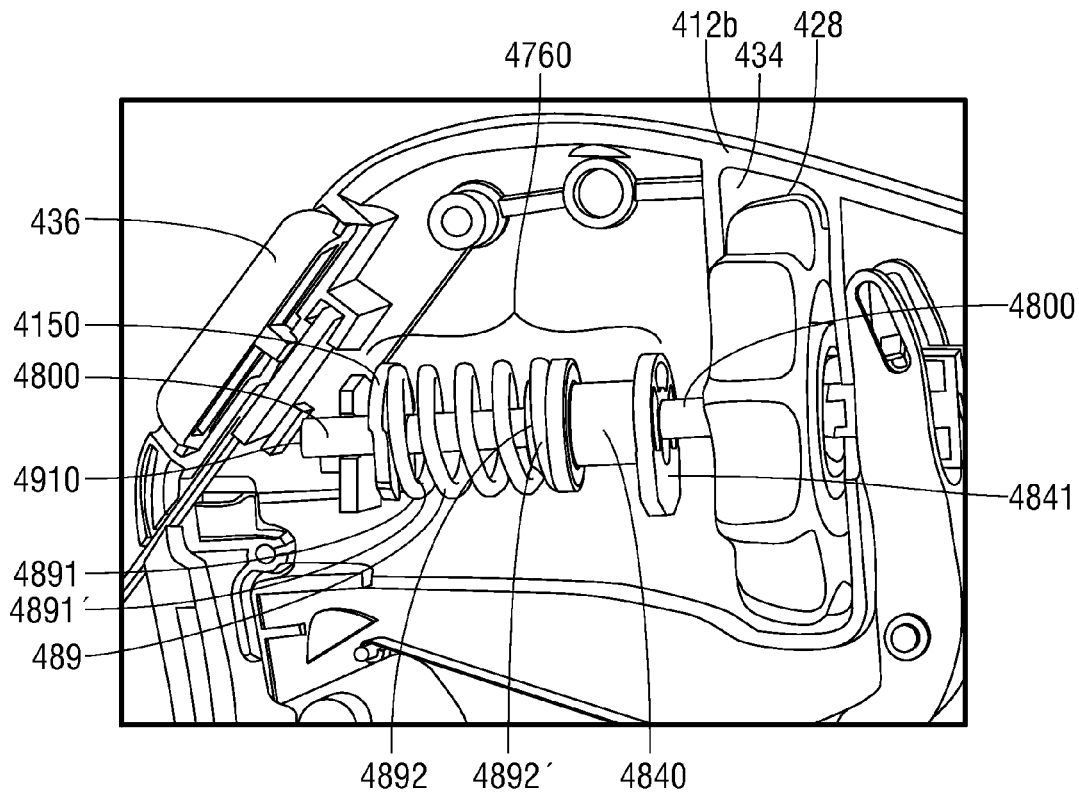
FIG. 17 is a partial, side view of a proximal portion of the jaw actuation mechanism of FIG. 16 depicting, without the movable handle, an alternate embodiment of the connection between the jaw actuation mechanism and the jaw drive rod mechanism for imparting longitudinal movement to the jaw drive rod.
Figure 18:
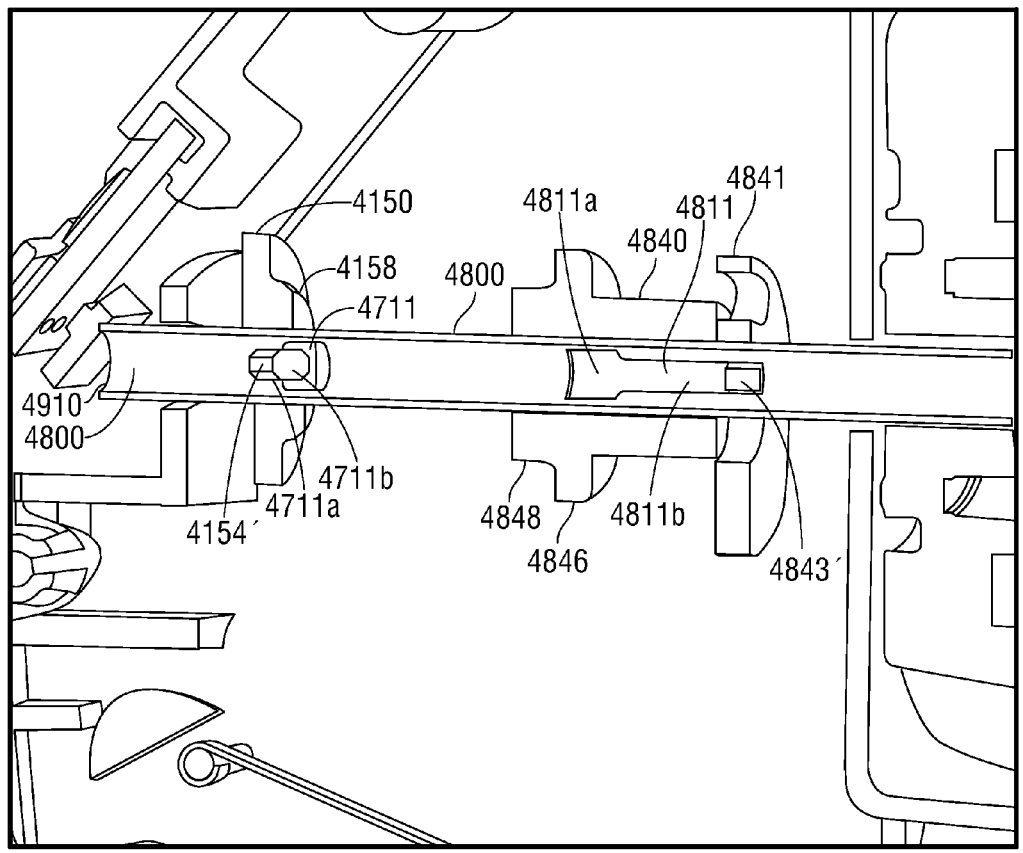
FIG. 18 is a cross-sectional, side view of an inner shaft member illustrating apertures in the inner shaft member and engagement of a drive collar and stop members on the inner shaft member.

Referring also to FIG. 17, the clevis 478 of movable handle 422 illustrated in FIG. 16 covers a portion of the connection mechanism 4760. As best illustrated in FIG. 17, where the clevis 478 of movable handle 422 is not illustrated, connection mechanism 4760 includes an inner shaft member 4800 that is configured to extend at least partially through an elongated shaft member such as elongated shaft member 416 of surgical instrument 400. Inner shaft member 4800 defines proximal end 4910 and a distal end (not explicitly shown but located in the direction of arrow 4912 in FIG. 22 and similarly to slots 472a and 472b in inner shaft 480 in FIG. 3A). The inner shaft member 4800 is selectively movable in a longitudinal direction, such as defined by axis "A"-"A" in FIG. 1, with respect to the elongated shaft 416. As described in more detail below, connection mechanism 4760 also includes a drive collar member 4840, a drive collar stop member 4841 and an inner shaft stop member 4150.

As best illustrated in FIGS. 18, 22, 24A, 24B and 24C, inner shaft member 4800 includes at least one aperture, e.g., at least distal locking slot 4811 or additionally, as shown, at least distal locking slot 4812, that is defined in the inner shaft member 4800. The distal locking slots 4811, 4812 extend partially along the longitudinal direction (axis "A"-"A") of the inner shaft member 4800 and are disposed distally from the proximal end 4910.

The inner shaft member 4800 is configured such that the inner shaft member 4800 enables drive collar member 4840 to be disposed to slide on the inner shaft member 4800 and movable along the longitudinal direction (axis "A"-"A") of the inner shaft member 4800. In one embodiment, the drive collar member 4840 is reciprocally movable along the longitudinal direction (axis "A"-"A") of the inner shaft member 4800.

The distal locking slots 4811, 4812 may be configured in an L-shape, or as shown in FIGS. 18, 22, 24A, 24B and 24C in a T-shape having proximal sections 4811a, 4812a and distal sections 4811b, 4812b configured such that the open area of the proximal sections 4811a, 4812a is greater than the open area of the distal sections 4811b, 4812b. Such a configuration of the locking slots 4811, 4812 enables a drive collar stop member 4841 to be disposed to slide on the inner shaft member 4800 such that the drive collar stop member 4841 moves first distally in a direction along the longitudinal axis "A"-"A" defined by the inner shaft member 4800 to approach the distal locking slots 4811, 4812 (see arrow E1 in FIG. 24B). Once slid proximate to locking slots 4811, 4812, the drive collar stop member 4841 moves in a direction relative to the longitudinal direction defined by axis "A"-"A" by shifting or dropping into engagement (see arrow E2 in FIG. 24B) first with the proximal sections 4811a, 4812a and then with the distal sections 4811b, 4812b (see arrow E3 in FIG. 24B) to limit further longitudinal motion of the drive collar member 4840 in the direction of the proximal end 4912 of the inner shaft member 4800. In one embodiment, the drive collar stop member 4841 is reciprocally movable or slidable along the longitudinal axis "A"-"A" defined by the inner shaft member 4800.

Figure 20A:
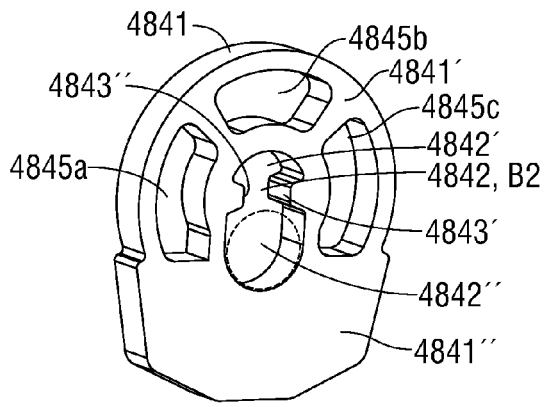
FIG. 20A is a perspective view of the drive collar stop member of FIGS. 16-18.
Figure 20B:
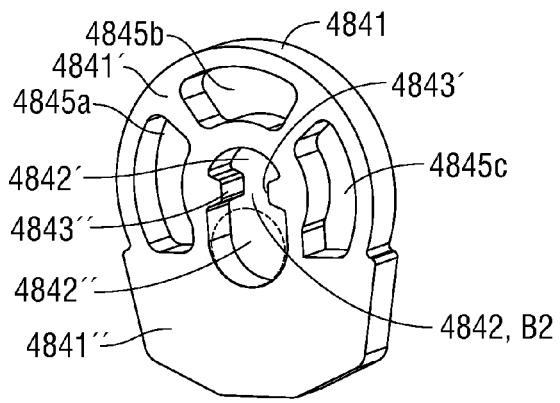
FIG. 20B is another perspective view of the drive collar stop member of FIGS. 16-18.
Figure 23:
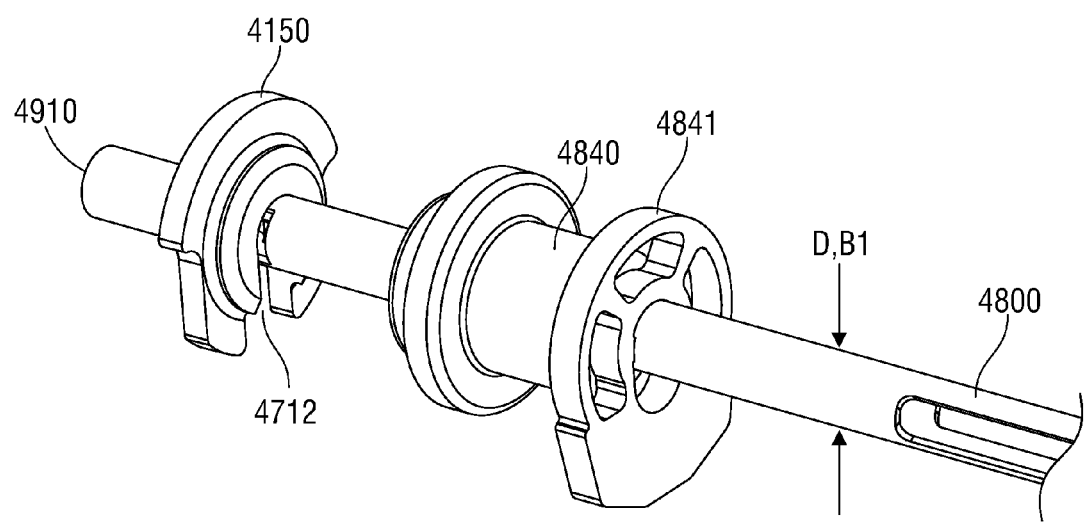
FIG. 23 is a perspective view of the inner shaft member and drive collar and stop members on the inner shaft member.

As best illustrated in FIG. 23, the inner shaft member 4800, having, for example, a circular cross-sectional configuration with a diameter D, therefore defines a first cross-sectional area B1. As best illustrated in FIGS. 20A and 20B, the drive collar stop member 4841 defines a central aperture 4842 having a second cross-sectional area B2. The second cross-sectional area B2 exceeds the first cross-sectional area B1 of the inner shaft member 4800 so as to define an upper portion 4842' of the second cross-sectional area B2 and a lower portion 4842" of the second cross-sectional area B2. The reduced area of the first cross-sectional area B1 results from the fact that, within the upper portion 4842', the drive collar stop member 4841 defines at least one projection, e.g., as illustrated two projections 4843', 4843", that project inwardly to reduce the upper portion 4842' of the second cross-sectional area B2 as compared to the lower portion 4842".

Thereby, as best illustrated in FIGS. 20A, 20B, 24A, 24B and 24C, the drive collar stop member 4841 retains the inner shaft member 4800 in the lower portion 4842" of the second cross-sectional area B2 as the drive collar stop member 4841 moves distally along the longitudinal direction between the proximal end 4910 of the inner shaft member 4800 and the distal locking slots 4811, 4812.

As described above with respect to FIGS. 18, 22, 24A, 24B and 24C, the drive collar stop member 4841 moves distally along the longitudinal direction (see FIG. 24B, arrow E1) to the distal locking slots 4811, 4812. When slid proximate to locking slots 4811, 4812, the drive collar stop member 4841 drops or shifts (see FIG. 24B, arrow E2) to a position wherein the projections 4843', 4843" engage first with the proximal sections 4811a, 4812a and then with the distal sections 4811b, 4812b (see FIG. 24B, arrow E3). Once the projections 4843', 4843" move distally within the distal sections 4811b, 4812b along the entire length of the distal sections 4811b, 4812b, drive collar stop member 4841 then limits further longitudinal motion of the drive collar member 4840 in the direction of the proximal end 4912 of the inner shaft member 4800.

In one embodiment, as best illustrated in FIGS. 20A, 20B, 23 and 24A, 24B and 24C, the drive collar stop member 4841 defines at least one portion 4841' having a weight density differing from at least another portion 4841" having another weight density. The shift of the drive collar stop member 4841 is effected by the difference in weight densities. More particularly, in the exemplary embodiment described herein, portion 4841' defines an upper portion of the drive collar stop member 4841 and portion 4841" defines a lower portion of the drive collar stop member 4841. The upper portion 4841' defines, for example, three apertures 4845a, 4845b and 4845c that are disposed, respectively, as arcuate segments forming a generally concentric configuration around the central aperture 4842.

In contrast, the lower portion 4841" is a solid member such that the weight density exceeds the weight density of the upper portion 4841' that defines the apertures 4845a, 4845b, 4845c. In this manner, as described above, the difference in weight densities effects the movement or shifting of the drive collar member 4841 in a direction relative to the longitudinal axis "A"-"A" defined by the inner shaft member 4800 (see FIG. 24B, arrow E2) to become engaged first with the proximal sections 4811a, 4812a and then with the distal sections 4811b, 4812b to limit further longitudinal motion of the drive collar member 4840 in the direction of the proximal end 4912 of the inner shaft member 4800 (see FIG. 25, arrows E1 and E3). As can be appreciated, this facilitates alignment and assembly during manufacturing.

As best illustrated in FIGS. 21A, 21B, 24A, 24B and 24C, drive collar member 4840 may be configured as a cylindrical member 4844 defining a central aperture 4844' having a diameter D' that is greater than diameter D of inner shaft member 4800 (see FIG. 23) so as to enable the drive collar 4840 to be mounted on the inner shaft member 4800 and reciprocally slide and move along the inner shaft member 4800.

Referring again to FIGS. 18, 22, 24A, 24B and 24C, FIGS. 18, 22, 24A, 24B and 24C best illustrate the inner shaft member 4800 includes at least one additional aperture, e.g., at least proximal locking slot 4711, or additionally at least proximal locking slot 4712 as shown, that is defined in the inner shaft member 4800. The proximal locking slots 4711, 4712 extend partially along the longitudinal direction (axis "A"-"A") of the inner shaft member 4800 and may be disposed proximally from the one or more apertures, e.g., distal locking slots 4811, 4812, that are disposed distally from the proximal end 4910.

The one or more proximal locking slots 4711, 4712 are configured to enable inner shaft stop member 4150 to be disposed to slide on the inner shaft member 4800 and to be movable along the longitudinal direction (axis "A"-"A") of the inner shaft member 4800. Inner shaft stop member 4150 is disposed proximally of the drive collar member 4840 and on the inner shaft member 4800.

The one or more proximal locking slots 4711, 4712 are also disposed proximally of the drive collar member 4840. The one or more proximal locking slots 4711, 4712 are configured to enable the inner shaft stop member 4150 to engage in the proximal locking slots 4711, 4712 and to limit movement of the inner shaft member 4800 along the longitudinal axis "A"-"A" following insertion of spring member 489 on the inner shaft member 4800 between the drive collar member 4840 and the inner shaft stop member 4150. The spring member 489 defines a proximal end 4891 and a distal end 4892.

The one or more proximal locking slots 4711, 4712 may be configured in an L-shape, or as shown in FIGS. 18, 22, 24A, 24B and 24C in a T-shape having proximal sections 4711a, 4712a and distal sections 4711b, 4712b configured such that the open area of the proximal sections 4711a, 4712a is less than the open area of the distal sections 4711b, 4712b.

As described in more detail below with respect to FIGS. 19A and 19B, such a configuration of the locking slots 4711, 4712 enables the inner shaft stop member 4150 to limit further axial movement of the inner shaft member 4800. More particularly, the inner shaft stop member 4150 is disposed to slide on the inner shaft member 4800 first in a direction relative to the longitudinal axis "A"-"A" defined by the inner shaft member 4800 (see FIG. 24B, arrow F1) to become engaged first with the one or more distal portions 4711b, 4712b. Following engagement with the one or more distal portions 4711b, 4712b, the inner shaft stop member 4150 then moves proximally in a direction along the longitudinal axis "A"-"A" defined by the inner shaft member 4800 (see FIG. 24B, arrow F2) to engage the one or more proximal portions 4711a, 4712a of the proximal locking slots 4711, 4712 following insertion of the spring member 489, in a compressed configuration, on the inner shaft member 4800 between the drive collar member 4840 and the inner shaft stop member 4150. Extension of the spring member 489 pushes inner shaft stop member 4150 proximally into the proximal portions 4711a, 4712a to limit movement of the inner shaft member 4800 along the longitudinal axis "A"-"A".

Figure 24A:
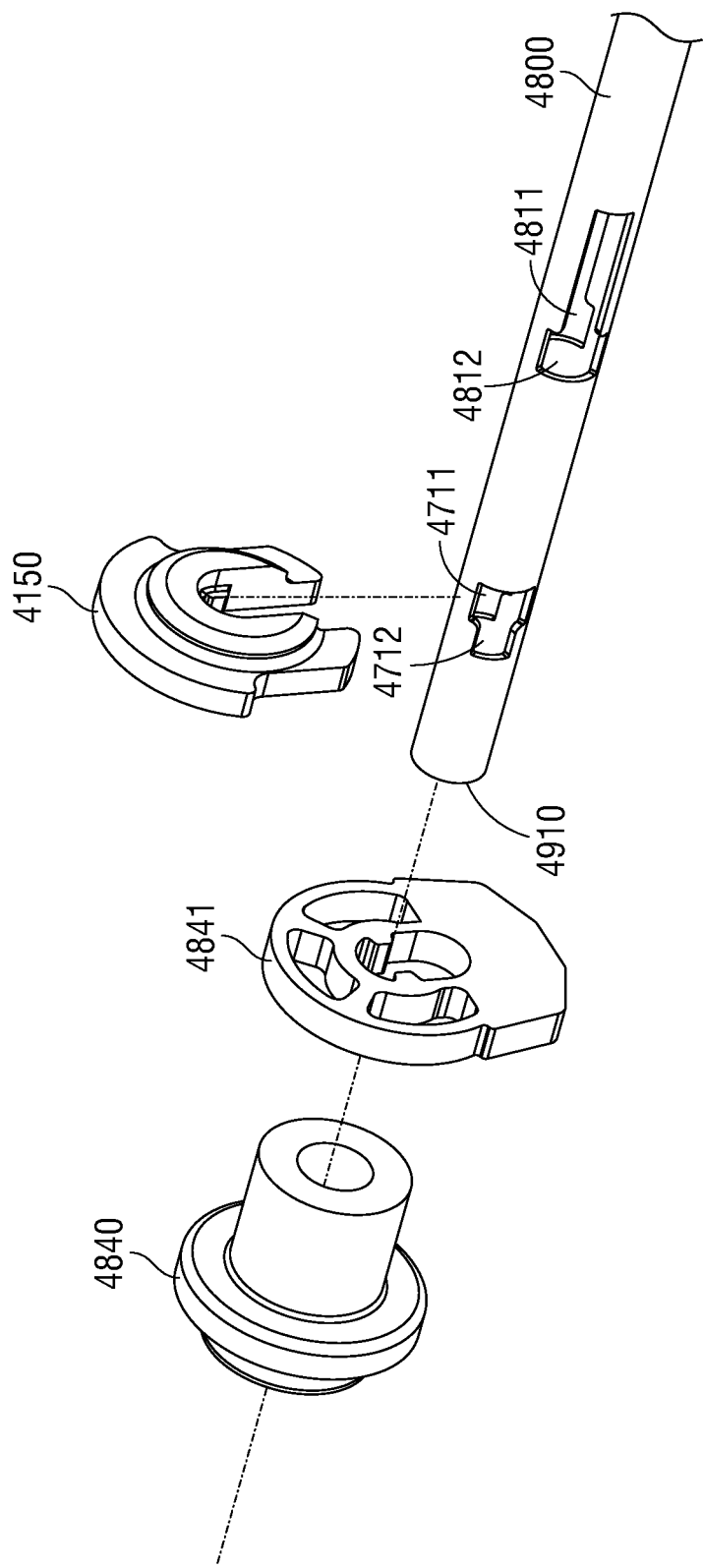
FIG. 24A is an exploded view of the inner shaft member and drive collar and stop members with respect to the inner shaft member.
Figure 24B:
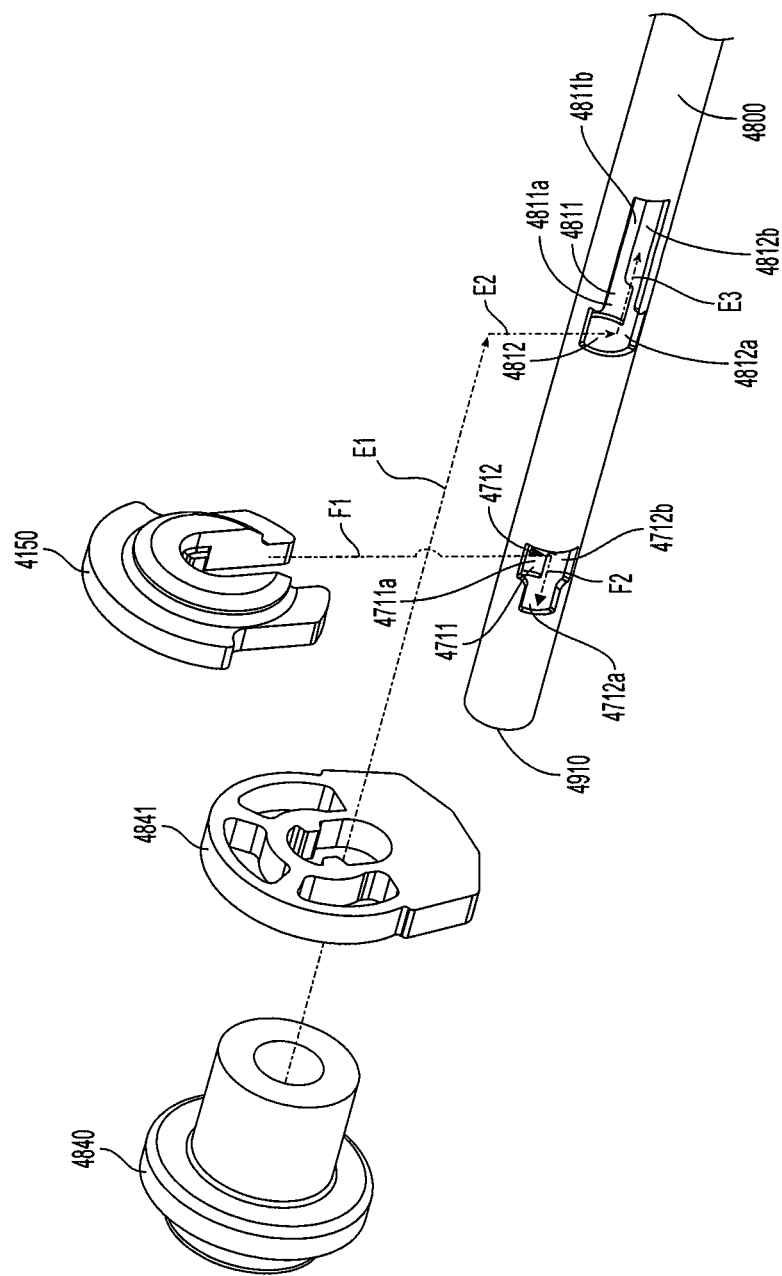
FIG. 24B is an alternate exploded view of the inner shaft member and drive collar and stop members with respect to the inner shaft member as illustrated in FIG. 24A which includes directional arrows to illustrate the movement of the drive collar and stop members with respect to the apertures in the inner shaft member.
Figure 24C:
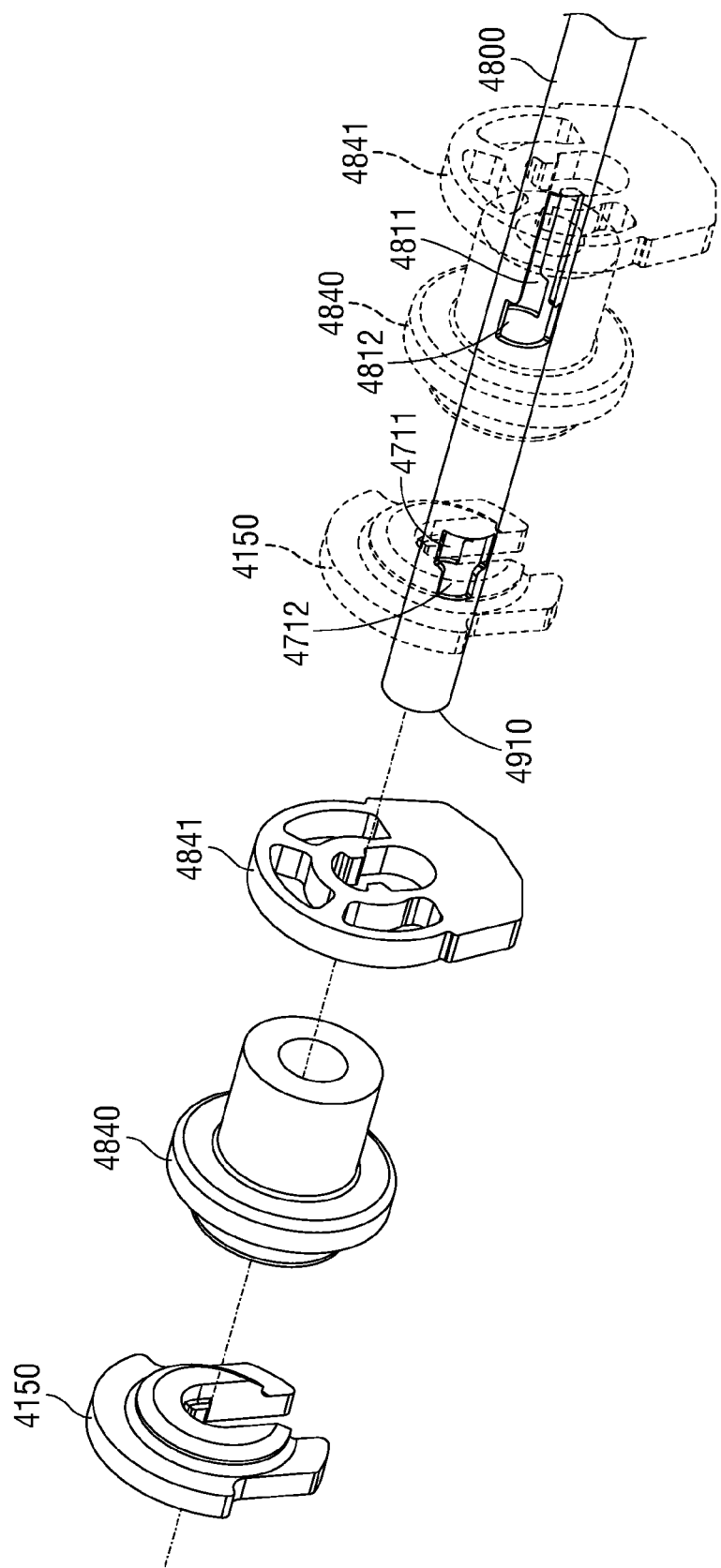
FIG. 24C is another exploded view of the inner shaft member and drive collar and stop members with respect to the inner shaft member.

In one embodiment, the direction relative to the longitudinal axis "A"-"A" includes a direction transverse to or crossing the longitudinal axis "A"-"A", such as vertically downward as shown by arrow F1 in FIG. 24B.

Figure 19A:
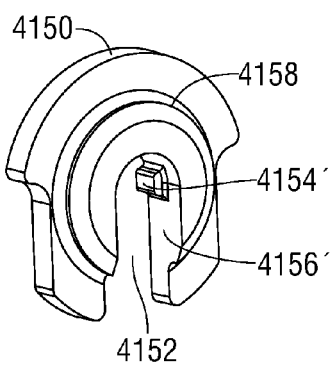
FIG. 19A is a perspective view of the inner shaft stop member of FIGS. 16-18.
Figure 19B:
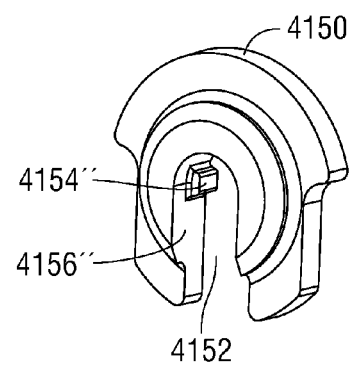
FIG. 19B is another perspective view of the inner shaft stop member of FIGS. 16-18.

As best shown in FIGS. 19A and 19B, the inner shaft stop member 4150 may engage the one or more proximal locking slots 4711, 4712 via an aperture 4152 defined by the inner shaft stop member 4150 to impart a generally U-shaped configuration to the inner shaft stop member 4150. At least one projection, e.g., projections 4154' and 4154" that are disposed on opposing inner surfaces 4156', 4156", project inwardly within aperture 4152 and effect the engagement of the inner shaft stop member 4150 with the one or more proximal portions 4711a, 4712a of the proximal locking slots 4711, 4712, respectively, to limit further proximal axial movement of the inner shaft stop member 4150. In one embodiment, the inner shaft stop member 4150 is reciprocally movable along the longitudinal axis "A"-"A" of the inner shaft member 4800.

Figure 21A:
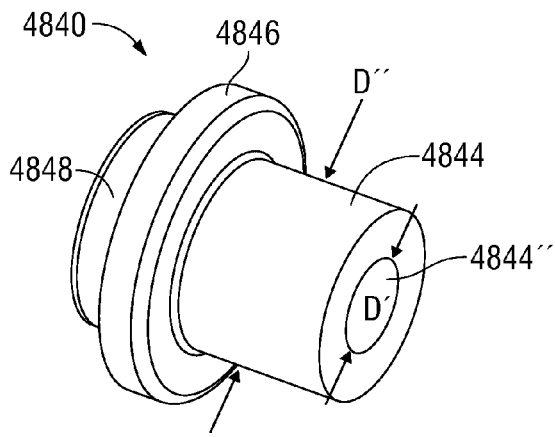
FIG. 21A is a perspective detail view of the drive collar of FIGS. 17-18.
Figure 21B:
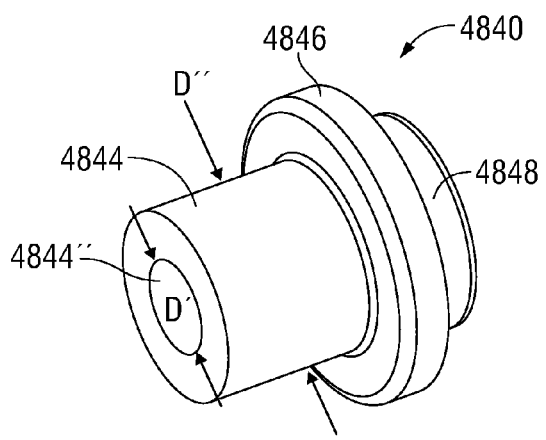
FIG. 21B is another perspective detail view of the drive collar of FIGS. 17-18.
Figure 22:
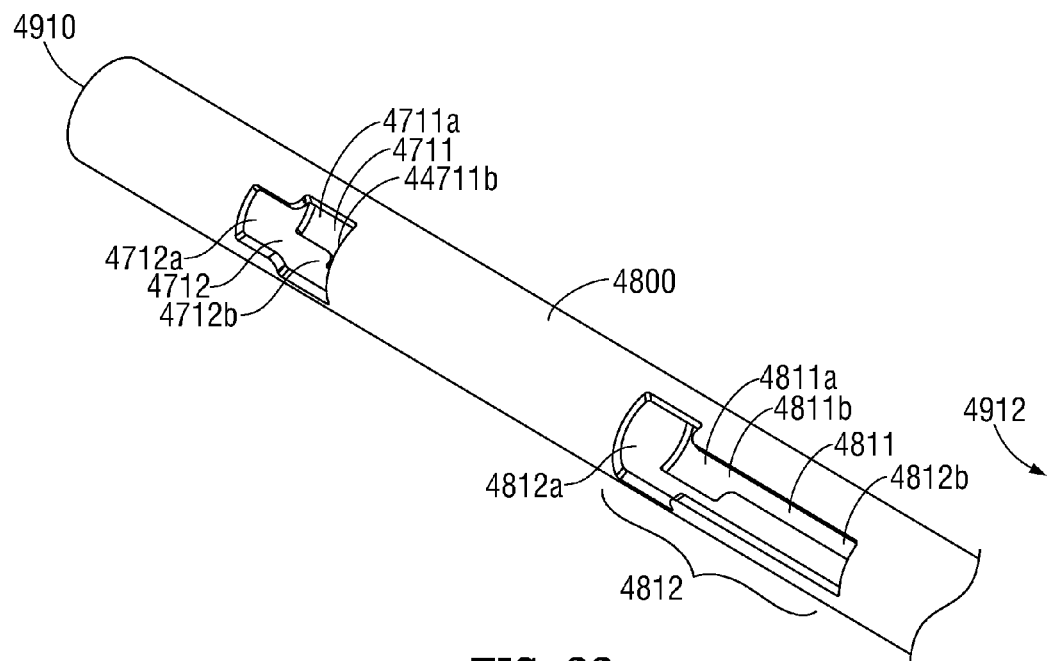
FIG. 22 is a perspective view of the apertures in the inner shaft member of FIG. 18.

As best illustrated in FIGS. 21A and 21B, the drive collar member 4840 may include a proximal rim 4846 that extends concentrically around, and projects radially from, outer diameter D" of the cylindrical member 4844 of drive collar member 4840.

The drive collar member 4840 may further include a projection 4848 that extends proximally from the drive collar member 4840 and which is configured to engage in an aperture 4892' defined in the distal end 4892 of the spring member 489 when the spring member 489 is inserted on the inner shaft member 4800 between the drive collar member 4840 and the inner shaft stop member 4150 (see FIG. 17).

In a similar manner, as best illustrated in FIGS. 17, 19A and 19B, the inner shaft stop member 4150 may further include a projection 4158 that extends distally from the inner shaft stop member 4150 and is configured to engage in an aperture 4891' defined in the proximal end 4891 of the spring member 489 when the spring member 489 is inserted on the inner shaft member 4800 between the drive collar member 4840 and the inner shaft stop member 4841.

Figure 25:
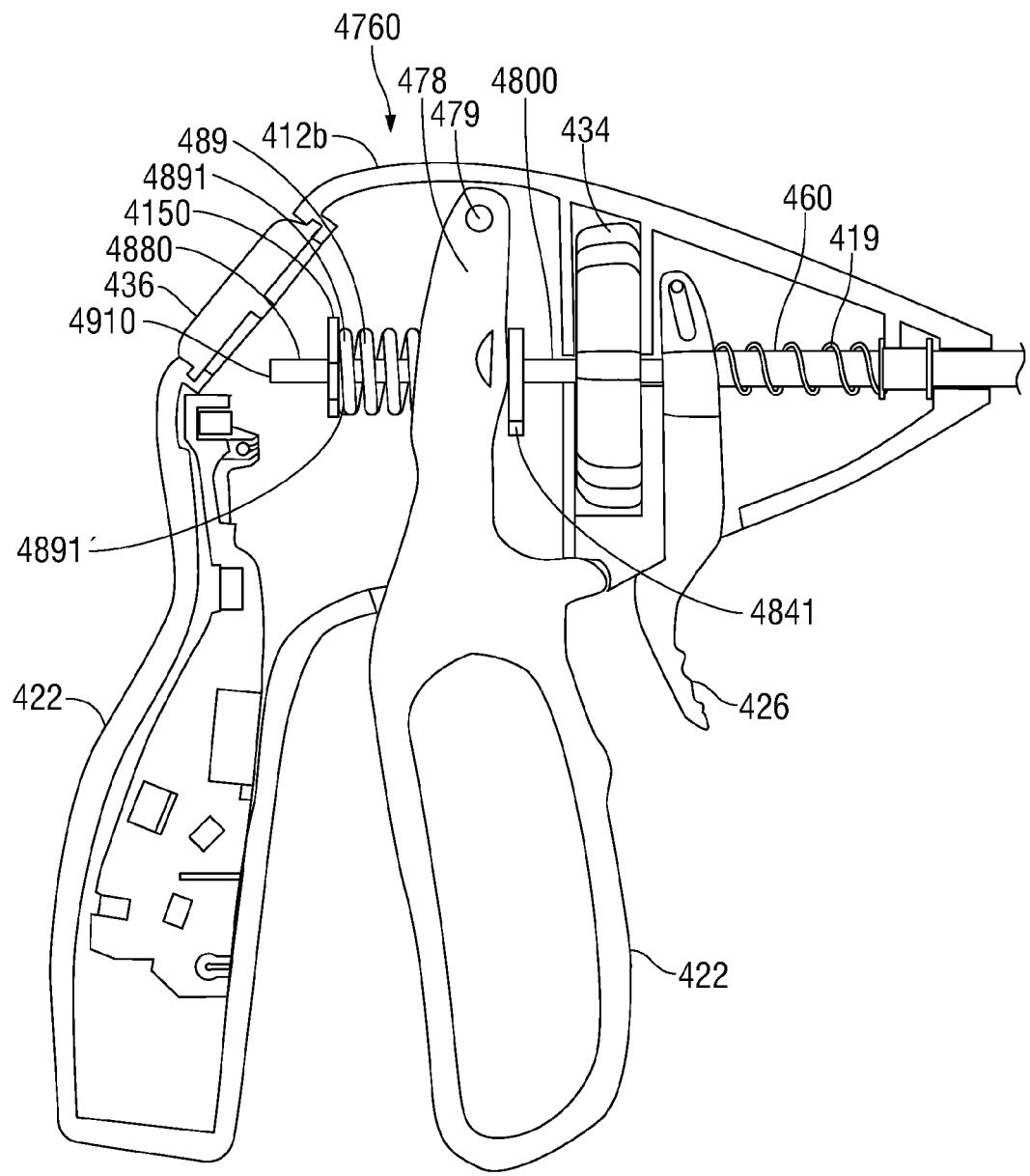
FIG. 25 is a cutaway view of an electrosurgical forceps that includes the inner shaft member and drive collar and stop members on the inner shaft member of FIGS. 16-24C.

As best illustrated in FIG. 25, the engagement of the proximal and distal ends 4891 and 4892 of the spring member 489 in the manner described enhances the ability of the connection mechanism 4760 to deliver a consistent axial force by reducing the probability that the spring member 489 will become misaligned with respect to the longitudinal axis "A"-"A". The engagement of the drive collar stop member 4841 and the inner shaft stop member 4150 in the manner described further enhances the ability of the connection mechanism 4760 to deliver a consistent axial force by further reducing the probability that the spring member 489 will become misaligned with respect to the longitudinal axis "A"-"A". Therefore, the connection mechanism 4760 yields a simplified spring load mechanism for delivering shaft load of a surgical instrument.

The foregoing description of FIGS. 16-25 also describes a method of manufacturing the connection mechanism 4760 for a surgical instrument to yield at least the same advantages as described above. As best shown in FIGS. 18, 22, 24A, 24B, and 24C, the method includes moving the drive collar stop member 4841 longitudinally along inner shaft member 4800 (e.g., in the direction of axis "A"-"A"), engaging the drive collar stop member 4841 in at least one aperture defined in the inner shaft member 4800, e.g., distal locking slot 4811 or additionally at least distal locking slot 4812, to limit further longitudinal movement of the drive collar stop member 4841, and moving drive collar member 4840 longitudinally along the inner shaft member 4800 until the drive collar stop member 4840 limits further longitudinal movement of the drive collar member 4840. The method may include moving the drive collar stop member 4841 in the direction relative to the longitudinal axis "A"-"A" so as to engage by shifting or dropping, e.g., see FIG. 24B, arrow E2, into one or both of the distal locking slots 4811, 4812 to limit further longitudinal movement of the drive collar stop member 4841.

As best illustrated in FIGS. 20A, 20B, 24A, 24B and 24C, the method may include retaining the inner shaft member 4800 in the lower portion 4842" of the aperture 4842 defined in the drive collar stop member 4841 as the drive collar stop member 4841 moves distally along the longitudinal direction "A"-"A" of the inner shaft member 4800.

The method may include limiting further longitudinal motion of the drive collar member 4840 in the direction of the proximal end 4912 of the inner shaft member 4800 by engaging the drive collar stop member 4841 with the one or more apertures such as distal locking slots 4811, 4812. This engaging may be effected by shifting the drive collar stop member 4841 in a direction relative to the longitudinal movement of the drive collar stop member 4841, e.g., by shifting or dropping into engagement (see FIG. 24B, arrow E2) first with the proximal sections 4811a, 4812a and then with the distal sections 4811b, 4812b (see FIG. 24B arrow E3) to limit further longitudinal motion of the drive collar member 4840 in the direction of the proximal end 4912 of the inner shaft member 4800.

In one embodiment, as best shown in FIGS. 20A, 20B, 24A, 24B and 24C, the drive collar stop member 4841 defines at least one portion having a weight density differing from at least another portion having another weight density, e.g., as explained above defining at least one portion 4841' having a weight density differing from at least another portion 4841" having another weight density. The method may include shifting of the drive collar stop member 4841 being effected by the difference in weight densities. For example, the method includes disposing the three apertures 4845a, 4845b and 4845c defined by the upper portion 4841', respectively, as arcuate segments forming a generally concentric configuration around the central aperture 4842.

In contrast, as can be appreciated from the description above, the method includes configuring the lower portion 4841" as a solid member such that the weight density exceeds the weight density of the upper portion 4841' that defines the apertures 4845a, 4845b, 4845c. Again as described above, the method includes effecting the movement or shifting of the drive collar member 4841 in a direction relative to the longitudinal axis "A"-"A" defined by the inner shaft member 4800 (see FIG. 24B, arrow E2) by the difference in weight densities to become engaged first with the proximal sections 4811a, 4812a and then with the distal sections 4811b, 4812b to limit further longitudinal motion of the drive collar member 4840 in the direction of the proximal end 4912 of the inner shaft member 4800 (see FIG. 24B, arrows E1 and E3). Again, as can be appreciated, this facilitates alignment and assembly during manufacturing.

As best shown in FIGS. 16, 17, 24A, 24B and 24C, the method may include inserting spring member 489 in a compressed configuration on the inner shaft member 4800 and moving the spring member 489 longitudinally along the inner shaft member 4800 to contact the drive collar member 4840 to limit further longitudinal movement of the spring member 489.

As best shown in FIG. 24B, the method may include moving inner shaft stop member 4150 in the direction relative to the longitudinal movement of the drive collar stop member 4841 along the inner shaft member (see FIG. 24B, arrow F1). The method may include also engaging the inner shaft stop member 4150 in the additional aperture, e.g., proximal locking slot 4711 or additionally proximal locking slot 4712, so as to limit longitudinal movement of the inner shaft stop member 4150 when the spring member 489 contacts the inner shaft stop member 4150 upon extending from the compressed configuration.

The method may include moving the inner shaft stop member 4150 in the direction of the longitudinal movement of the drive collar member (see FIG. 24B, arrow F2) to engage with the one or more additional apertures, e.g., proximal locking slots 4811 and 4812 to limit further longitudinal movement of the inner shaft member 4800.

As best illustrated in FIGS. 16, 17, 21A, 21B and 25, the method may include engaging the projection 4848 that extends proximally from the drive collar member 4840 within the aperture 4892' defined in the distal end 4892 of the spring member 489 when the spring member 489 is inserted on the inner shaft member 4800 between the drive collar member 4840 and the inner shaft stop member 4150. The method may also include engaging the projection 4158 that extends distally from the inner shaft stop member 4150 within the aperture 4891' defined in the proximal end 4891 of the spring member 489 again when the spring member 489 is inserted on the inner shaft member 4800 between the drive collar member 4840 and the inner shaft stop member 4150.

Referring particularly to FIGS. 19A and 19B, the method may include defining an aperture in the inner shaft stop member 4150 to impart a generally U-shaped configuration to the inner shaft stop member, e.g., defining aperture 4152 in inner shaft stop member 4150, and defining at least one projection projecting inwardly, e.g., projection 4154' and, in one embodiment, projection 4154" within the aperture 4152. The engaging of the at least one additional aperture, e.g., proximal locking slots 4711 and 4712, is effected by engaging the one or more projections 4154' and 4154", respectively, with the one or more additional apertures such as proximal locking slots 4711 and 4712.

As best illustrated in FIGS. 18, 22, 24A, 24b and 24C, those skilled in the art will recognize and understand that additional method of manufacturing steps may be directed to, for example, configuring the proximal sections 4711a, 4712a and distal sections 4711b, 4712b of the proximal locking slots 4711, 4712 such that the open area of the proximal sections 4711a, 4712a is less than the open area of the distal sections 4711b, 4712b, as well as to the configuring of the proximal sections 4811a, 4812a and distal sections 4811b, 4812b of the distal locking slots 4811, 4812 such that the open area of the proximal sections 4811a, 4812a is greater than the open area of the distal sections 4811b, 4812b. Those skilled in the art will also recognize that other analogous method of manufacturing steps may be directed to other features of the present disclosure as described above with respect to FIGS. 16-25.

The method of manufacturing in the manner described effects the engagement of the proximal and distal ends 4891 and 4892 of the spring member 489 which enhances the ability of the connection mechanism 4760 to deliver a consistent axial force by reducing the probability that the spring member 489 will become misaligned with respect to the longitudinal axis "A"-"A". The method of manufacturing in the manner described also effects the engagement of the drive collar stop member 4841 and the inner shaft stop member 4150 which further enhances the ability of the connection mechanism 4760 to deliver a consistent axial force by further reducing the probability that the spring member 489 will become misaligned with respect to the longitudinal axis "A"-"A". Therefore, the method of manufacturing connection mechanism 4760 yields a simplified spring load mechanism for delivering shaft load of a surgical instrument.

In one embodiment of the method of manufacturing, the drive collar stop member 4841 is installed on the inner shaft member 4800 by manually moving the drive collar stop member 4841 and the drive collar member 4840 along the inner shaft member 4800 to engage the drive collar stop member 4841 in the appropriate apertures as described above and also by manually moving inner shaft stop member 4150 vertically downward to engage in the appropriate apertures as described above. Alternatively, these same manufacturing steps may be performed automatically via mechanical or robotic mechanisms such as are already known in the art or to become known in the art.

Similarly, the spring member 489 may be installed on the inner shaft member 4800 manually or, alternatively, automatically via mechanical or robotic mechanisms such as are already known in the art or to become known in the art.

The method of manufacturing connection mechanism 4760 as described above is significantly advantageous over the prior art because the method does not require attaching a mandrel to the inner shaft member or attaching E-clips fasteners. Hence, there are considerable cost savings realized by eliminating the need to attach a mandrel to the inner shaft member and the material cost of the mandrel itself.

Since the apertures and other features of the inner shaft member may be cut directly into the inner shaft member, reduced tolerances and more precise dimensions may be realized.

The inner shaft member, the drive collar member, the drive collar stop member, the spring and the inner shaft stop member are assembled from the proximal end of the surgical instrument. The apertures such as the distal and proximal locking slots are configured and dimensioned to prevent incorrect insertion of the drive collar stop member into the proximal locking slots and incorrect insertion of the inner shaft stop member into the distal locking slots.

The method of manufacturing reduces part count as compared to connection mechanisms in prior art surgical instruments, which lowers costs and decreases assembly time. The weight imbalance of drive collar stop member allows the drive collar stop member to automatically slide on the inner shaft member during assembly always in the same orientation and lock together with the inner shaft member during assembly, thus saving time and assembly steps. The method of manufacturing also eliminates the need for through pins that can cut the electrical wires to the jaw members, and which increase assembly time and part count.

Additionally, the connection mechanism components, particularly the drive collar stop member and the inner shaft stop member, may be manufactured by the die-casting or powder metallurgy process, which is an inexpensive process for making components.

As a result, the method of manufacturing connection mechanism 4760 results in a connection mechanism 4760 that, for the reasons described above, yields a simplified spring load mechanism for delivering shaft load of a surgical instrument.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A method of assembling a surgical instrument, comprising:
    inserting a knife into a knife guide;
    positioning the knife and the knife guide within an inner shaft;
    moving a drive collar stop having a pair of opposing projections along a longitudinal axis defined through the inner shaft;
    engaging the pair of opposing projections of the drive collar stop within a corresponding first pair of opposing apertures defined in the inner shaft;
    moving a drive collar having a cylindrical member and a proximal rim disposed at a proximal end of the cylindrical member along the inner shaft to abut a free distal end of the cylindrical member with the drive collar stop and limit distal movement of the drive collar along the inner shaft;
    moving a spring along the inner shaft to engage the drive collar and limit distal movement of the spring;
    compressing the spring;
    moving an inner shaft stop having a pair of opposing projections transverse to the longitudinal axis defined through the inner shaft; and
    engaging the pair of opposing projections of the inner shaft stop within a corresponding second pair of opposing apertures defined in the inner shaft proximal to the first pair of opposing apertures to limit proximal movement of the inner shaft and retain the spring between the inner shaft stop and the drive collar in a compressed condition.

2. The method according to claim 1, further comprising operably coupling the knife guide to the inner shaft.

3. A method of assembling a surgical instrument, comprising:
    inserting a knife into a knife guide;
    positioning the knife and the knife guide within an inner shaft;
    moving a drive collar stop having a pair of opposing projections along a longitudinal axis defined through the inner shaft;
    moving the drive collar stop transverse to the longitudinal axis to engage the pair of opposing projections of the drive collar stop within a proximal section of each of a corresponding first pair of opposing slots defined in the inner shaft;

moving the drive collar stop distally within the first pair of opposing slots to engage the opposing pair of projections of the drive collar stop within a distal section of each of the corresponding pair of opposing slots and limit further longitudinal movement of the drive collar stop;

moving a drive collar having a cylindrical member and a proximal rim disposed at a proximal end of the cylindrical member along the inner shaft to abut a free distal end of the cylindrical member with the drive collar stop and limit distal movement of the drive collar along the inner shaft;

moving a spring along the inner shaft to engage the drive collar and limit distal movement of the spring;

compressing the spring;

moving an inner shaft stop having a pair of opposing projections transverse to the longitudinal axis defined through the inner shaft to engage the pair of opposing projections of the inner shaft stop within a distal section of each of a corresponding second pair of opposing slots defined in the inner shaft proximal to the first pair of opposing slots; and moving the inner shaft stop proximally within the second pair of opposing slots to engage the pair of opposing projections of the inner shaft stop within a proximal section of each of the corresponding second pair of opposing slots to limit proximal movement of the inner shaft stop and retain the spring between the inner shaft stop and the drive collar in a compressed condition.

4. The method according to claim 3, further comprising operably coupling the knife guide to the inner shaft.

* * * * *